US010105524B2

(12) United States Patent
Meyer et al.

(10) Patent No.: US 10,105,524 B2
(45) Date of Patent: Oct. 23, 2018

(54) ARTICLE WITH HOLLOW MICRONEEDLES AND METHOD OF MAKING

(71) Applicant: 3M INNOVATIVE PROPERTIES COMPANY, St. Paul, MN (US)

(72) Inventors: Kenneth A. P. Meyer, White Bear Township, MN (US); Przemyslaw P. Markowicz, Woodbury, MN (US); Stanley Rendon, Eagan, MN (US); Robert L. W. Smithson, Mahtomedi, MN (US); Ryan Patrick Simmers, Fargo, ND (US)

(73) Assignee: 3M Innovative Properties Company, St. Paul, MN (US)

( * ) Notice: Subject to any disclaimer, the term of this patent is extended or adjusted under 35 U.S.C. 154(b) by 515 days.

(21) Appl. No.: 14/653,494

(22) PCT Filed: Dec. 13, 2013

(86) PCT No.: PCT/US2013/074943
§ 371 (c)(1),
(2) Date: Jun. 18, 2015

(87) PCT Pub. No.: WO2014/105458
PCT Pub. Date: Jul. 3, 2014

(65) Prior Publication Data
US 2015/0306363 A1    Oct. 29, 2015

Related U.S. Application Data

(60) Provisional application No. 61/746,198, filed on Dec. 27, 2012.

(51) Int. Cl.
A61M 37/00    (2006.01)
A61B 5/15    (2006.01)
(Continued)

(52) U.S. Cl.
CPC ... *A61M 37/0015* (2013.01); *A61B 5/150389* (2013.01); *A61B 5/150396* (2013.01);
(Continued)

(58) Field of Classification Search
CPC ...... A61M 37/0015; A61M 2037/0023; A61M 2037/003; A61M 2037/0038;
(Continued)

(56) References Cited

U.S. PATENT DOCUMENTS 4,489,033 A    12/1984    Uda et al.
4,515,543 A    5/1985    Hamner
(Continued)

FOREIGN PATENT DOCUMENTS

JP    2011-72695    4/2011
WO    WO 2000/35530    6/2000
(Continued)

OTHER PUBLICATIONS

Aoyagi, S. et al.; "Laser fabrication of high aspect ratio thin holes on biodegradable polymer and its application to a microneedle"; Sensors and Actuators A 139; 2007; pp. 293-302 (ISSN 0924-4247).
(Continued)

*Primary Examiner* — Nathan R Price
*Assistant Examiner* — Anh Bui
(74) *Attorney, Agent, or Firm* — Eric E. Silverman

(57) ABSTRACT

The present application provides articles (10) having a polymeric substrate (12) with a plurality of solid and/or hollow microneedles (20) extending therefrom. Each solid microneedle is formed by a molding process and the microneedle has body with first (30) and second cavities (40) extending therein. The hollow microneedles are formed by removing a portion of the polymeric material disposed between the first cavity and the second cavity. A method for determining the location of a microneedle in an article
(Continued)

comprising solid microneedles is also provided. The method comprises directing electromagnetic radiation toward an article comprising a plurality of microneedles and imaging the article.

20 Claims, 6 Drawing Sheets

(51) Int. Cl.
  *B29C 69/00* (2006.01)
  *B29L 31/00* (2006.01)
(52) U.S. Cl.
  CPC ...... *A61B 5/150984* (2013.01); *B29C 69/001* (2013.01); *A61M 2037/003* (2013.01); *A61M 2037/0023* (2013.01); *A61M 2037/0038* (2013.01); *A61M 2037/0046* (2013.01); *A61M 2037/0053* (2013.01); *A61M 2037/0061* (2013.01); *B29L 2031/7544* (2013.01)
(58) Field of Classification Search
  CPC .. A61M 2037/0053; A61M 2037/0061; A61M 2037/0046; A61B 5/150984; A61B 5/150389; A61B 5/150396
  See application file for complete search history.

(56) References Cited

U.S. PATENT DOCUMENTS

| | | | |
|---|---|---|---|
| 6,091,975 | A | 7/2000 | Daddona et al. |
| 6,248,281 | B1 | 6/2001 | Abe et al. |
| 6,312,612 | B1 | 11/2001 | Sherman et al. |
| 6,379,324 | B1 | 4/2002 | Gartstein et al. |
| 6,451,240 | B1 | 9/2002 | Sherman et al. |
| 6,558,361 | B1 | 5/2003 | Yeshurun |
| 6,815,360 | B1 | 11/2004 | Canham et al. |
| 6,881,203 | B2 | 4/2005 | Delmore et al. |
| 7,648,484 | B2 | 1/2010 | Yeshurun et al. |
| 8,088,321 | B2 | 1/2012 | Ferguson et al. |
| 2005/0261631 | A1 | 11/2005 | Clarke et al. |
| 2008/0088066 | A1 | 4/2008 | Ferguson et al. |
| 2009/0099537 | A1 | 4/2009 | DeVoe et al. |
| 2009/0318833 | A1* | 12/2009 | Lim ..................... A61M 5/329 600/573 |
| 2011/0073560 | A1 | 3/2011 | Yeshurun et al. |
| 2011/0213335 | A1 | 9/2011 | Burton et al. |
| 2012/0041337 | A1 | 2/2012 | Ferguson et al. |
| 2012/0123387 | A1 | 5/2012 | Gonzalez et al. |
| 2012/0258284 | A1 | 10/2012 | Rendon |
| 2013/0218084 | A1 | 8/2013 | Tamaru et al. |

FOREIGN PATENT DOCUMENTS

| | | |
|---|---|---|
| WO | WO 2005/123173 | 12/2005 |
| WO | WO 2006/055771 | 5/2006 |
| WO | WO 2006/055802 | 5/2006 |
| WO | WO 2006/108185 | 10/2006 |
| WO | WO 2007/002521 | 1/2007 |
| WO | WO 2007/002522 | 1/2007 |
| WO | WO 2007/070004 | 6/2007 |
| WO | WO 2010/117602 | 10/2010 |
| WO | WO 2012/057270 | 5/2012 |
| WO | WO 2012/074576 | 6/2012 |
| WO | WO 2012/122162 | 9/2012 |

OTHER PUBLICATIONS

Davis, S.P. et al.; "Fabrication and Characterization of Laser Micromachines Hollow Microneedles" Transducers '03—12$^{th}$ International Conference on Solid State Sensors, Actuators and Microsystems; 2003; pp. 1435-1438.

Martanto, W. et al.; "Side-Opening Hollow Microneedles for Transdermal Drug Delivery"; School of Chemical and Biomolecular Engineering, School of Electrical and Computer Engineering, Georgia Institute of Technology, Atlanta, GA;(date unknown but believed to be prior to the date of the filing of the present application).

Trichur, R. et al.; "Development of Plastic Microneedles for Transdermal Interfacing Using Injection Molding Techniques"; Micro Total Analysis Systems; vol. 1; 2002; pp. 395-397.

Martanto, W.; Thesis entitled "Microinjection into Skin Using Microneedles"; Georgia Institute of Technology; Aug. 2005; 185 pgs.

Jiang, N.; Thesis entitled "Ocular Drug Delivery Using Microneedles"; Georgia Institute of Technology; Dec. 206; 157 pgs.

"Laser Drilling Process" from Prima Industrie obtained from internet Oct. 1, 2013 from URL http://www.prima-na.com/pages/44_laser_drilling.cfm 3 pgs.

* cited by examiner

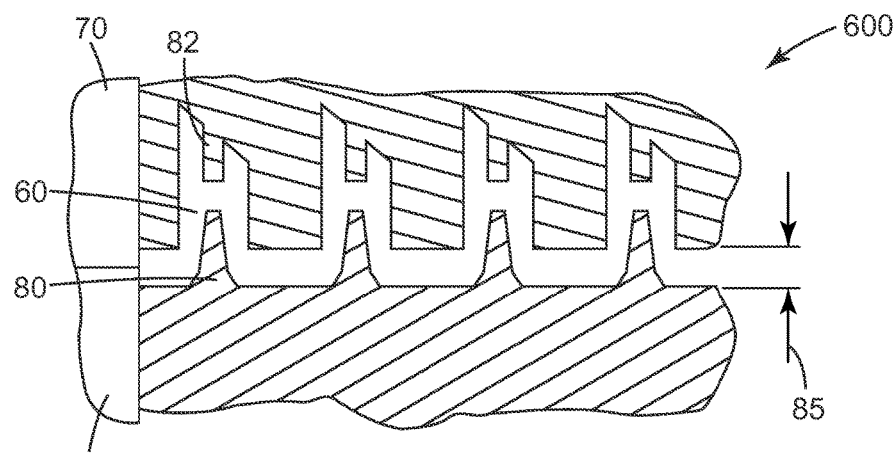
Fig. 6
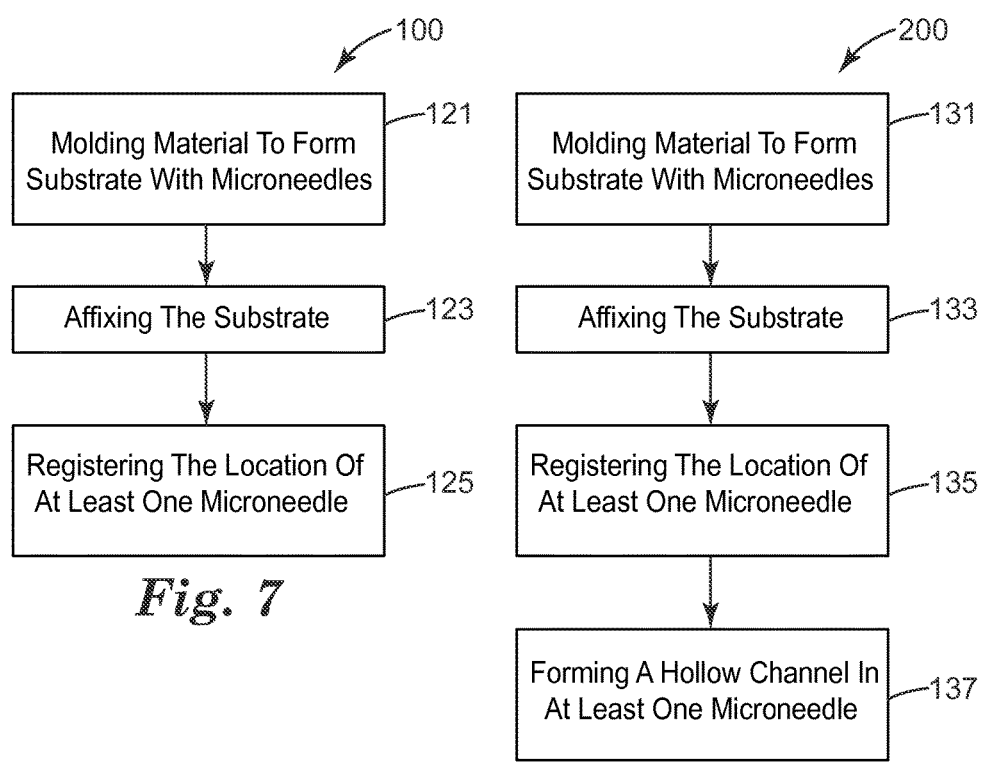
Fig. 7
Fig. 8

ARTICLE WITH HOLLOW MICRONEEDLES AND METHOD OF MAKING

CROSS REFERENCE TO RELATED APPLICATIONS

This application is a national stage filing under 35 U.S.C. 371 of PCT/US2013/074943, filed Dec. 13, 2013, which claims priority to U.S. Provisional Patent Application No. 61/746,198, filed Dec. 27, 2012, the disclosure of which is incorporated by reference in its entirety herein.

BACKGROUND

Transdermal patches have long been used for the administration of small molecule lipophilic drugs that can be readily absorbed through the skin. This non-invasive delivery route is advantageous for the administration of many drugs incompatible with oral delivery, as it allows for direct absorption of the drug into the systemic circulation, bypassing both the digestive and hepatic portal systems which can dramatically reduce the bioavailability of many drugs. Transdermal delivery also overcomes many of the challenges associated with subcutaneous injection by greatly reducing patient discomfort, needle anxiety, risk of accidental injury to the administrator and issues surrounding sharps disposal.

Despite these many advantages, transdermal delivery of drugs is confined to classes of molecules compatible with absorption through the skin. Delivery of small molecule salts and therapeutic proteins are not typically viable with traditional transdermal delivery, as the skin provides an effective protective barrier to these molecules even in the presence of absorption-enhancing excipients.

Microneedle (including microblade) drug delivery devices have been proposed based on a wide variety of designs and materials. Some are solid, e.g., with drug coated thereon, and others are hollow, e.g., with drug delivered from a reservoir. Some are made of metal, whereas others are etched from silicon material, and still others are made of plastics such as polycarbonate.

The number, size, shape, and arrangement of the microneedles also vary considerably. Some have a single needle, while others, especially solid microneedles, have hundreds of needles per array. Most range in size from 100 microns to 2 mm.

Microneedles have shown promise for delivery drugs intradermally and transdermally, particularly where a relatively small quantity of drug is needed such as in the case of vaccines or potent drugs.

One of the desired benefits of microneedles is of course to replace, where appropriate, conventional hypodermic needles, which can cause anxiety and/or pain for many patients. There are also benefits to delivering some drugs, e.g., vaccines, into the skin rather than via intramuscular injection. However, microneedle delivery systems often have been seen as providing quite low rates of delivery, thus limiting the usefulness of such systems by requiring either small quantities of drug formulation to be used or long delivery times. For example, typical intradermal infusion using microneedles has been documented with slow infusion rates of less than 30 mcL/hour, and low infusion volumes less than 200 mcL.

SUMMARY

Because microneedle structures are inherently very small, passageways (or channels) formed in the microneedles are limited in size. As a result, microneedles and the passageways of the microneedles can be difficult to manufacture. Further, it can be difficult using known molding processes to mass-produce polymeric substrates having a plurality of polymeric microneedles wherein microneedle has a cavity or a through-hole configured to deliver a substance (e.g., a medicament). The present inventors have determined that known microneedle molding processes all have certain limitations that make it difficult to form hollow microneedles with aspect ratios higher than about 2:1. The inventive methods provide precise, reproducible processes for making articles with a plurality of hollow microneedles that have high aspect ratios.

There is a need for accurately determining and positioning the location of the cavities and/or passageways within the microneedles. The present inventors recognize a need and provide a method for accurately determining and positioning the location of the cavities and/or passageways within a microneedle so that the microneedle can be used in a process to manufacture high-fidelity (i.e., replication that results in an article with near identical microneedle shape and cavity or passageway shape), low cycle time, and high volume (i.e., molds can be used repeatedly) hollow microneedle arrays. In addition, the hollow microneedles can comprise relatively large-bore channels that provide a high infusion rate to deliver a medicament into a treatment site.

In one aspect, the present disclosure provides an article. The article can comprise a substrate having first side and second side opposite the first side. The first side comprises a first major surface that defines a base from which at least one microneedle extends. The at least one microneedle comprises a body, a tip and a first cavity extending into the body. The first cavity comprises an opening on the first side and a first terminus. The second side comprises a second major surface comprising a second cavity that extends into the body of the at least one microneedle. The second cavity comprises a second opening on the second side, and a second terminus. The first terminus is spaced apart from the second terminus. A straight line passing through the substrate can enter the substrate at a first point in the second cavity and exit the substrate at a second point in the first cavity. In any embodiment, a shortest distance between the first cavity terminus and the second cavity terminus can be about 1 micron to about 500 microns, inclusive.

In another aspect, the present disclosure provides an article. The article comprises a substrate having first side and second side opposite the first side, wherein the first side comprises a first major surface having at least one microneedle extending therefrom, the at least one microneedle comprising a body and a first opening, wherein the second side comprises a second major surface having a second opening. The article further comprises a channel extending from the first opening to the second opening, the channel having a first channel segment extending from the first opening, a second channel segment extending into the substrate from the second opening, and a third channel segment extending between the first channel segment and the second channel segment. The first channel segment has a first interior surface topology, the second channel segment has a second interior surface topology, and the third channel segment has a third interior surface topology. The third interior surface topology is optically distinguishable from the first interior surface topology. In any embodiment, the third interior surface topology can be optically distinguishable from the first interior surface topology and the second interior surface topology. In any of the above embodiments, the channel can be spaced apart from the tip of the microneedle.

In yet another aspect, the present disclosure provides a method. The method can comprise molding a material to form a substrate having a first side and a second side opposite the first side. The first side comprises a first major surface that defines a base from which a plurality of microneedles extend; wherein each microneedle of the plurality of microneedles comprises a body, a tip and a first cavity extending into the body. The second side comprises a second major surface that includes a plurality of second cavities, each second cavity extending into a body of one of the plurality of microneedles. A straight line passing through the substrate can enter the substrate at a first point in the first cavity and exit the substrate at a second point in the second cavity. The method further comprises affixing the substrate, registering a location of at least one microneedle, and forming a hollow channel through one of the plurality of microneedles, wherein forming a hollow channel comprises forming a channel between the first cavity and the second cavity. In any embodiment, registering a location of at least one microneedle can comprise registering the location of each microneedle of the plurality of microneedles. In any of the above embodiments, forming a hollow channel can comprise using an ablation process, a melting process, or a mechanical drilling process. In any of the above embodiments using an ablation process, the method further can comprise using a mask element to target the ablation process. In any of the above embodiments, the method further can comprise of imaging at least one microneedle of the plurality of microneedles.

In yet another aspect, the present disclosure provides a method. The method can comprise molding a material to form a substrate. The substrate can comprise a first major surface comprising a plurality of microneedles extending there from, each microneedle comprising a first cavity; and a second major surface opposite the first major surface, the second major surface comprising a plurality of second cavities. Molding the material comprises forming a thinned region between the first cavity and the second cavity. A straight line passing through the material can enter the substrate at a first point in the second cavity and exit the substrate at a second point in the first cavity. The method further can comprise directing electromagnetic radiation toward the first major surface and using an imaging device to capture an image of the second major surface or directing electromagnetic radiation toward the second major surface and using an imaging device to capture an image of the first major surface; and using the image to process two or more microneedles of the plurality of microneedles. In any embodiment, processing two or more microneedles can comprise creating through-hole between the first and second cavities of a plurality of microneedles or can comprise a composition to a plurality of microneedles.

As used herein, certain terms will be understood to have the meaning set forth below:

"Microneedle" refers to a specific structure (e.g., less than or equal to about 2000 microns in length) associated with an article. The microneedle has microscopic features and is designed for piercing the stratum corneum to facilitate the transdermal delivery of therapeutic agents or the sampling of fluids through the skin. By way of example, microneedles can include needle or needle-like structures, including microblades, as well as other structures capable of piercing the stratum corneum.

"Hollow microneedle" refers to a microneedle having a through-hole extending from a location on the microneedle spaced apart from the base to at least the base of the microneedle. Hollow microneedles include microneedles extending from a substrate having a through-hole extending all the way through the substrate.

"Solid microneedle" refers to a microneedle that does not have a through-hole extending from a location on the microneedle spaced apart from the base to at least the base of the microneedle. Solid microneedles may, however, have one or more cavities extending into, but not through, the body of the microneedle as described herein.

"Cavity" refers to a dead-end cavity such as a depression, crater, pit, pocket, sinus, or recess, for example, in the surface of a substrate.

The features and advantages of the present invention will be understood upon consideration of the detailed description of the preferred embodiment as well as the appended claims. These and other features and advantages of the invention may be described below in connection with various illustrative embodiments of the invention. The above summary of the present invention is not intended to describe each disclosed embodiment or every implementation of the present invention. The Figures and the detailed description which follow more particularly exemplify illustrative embodiments.

BRIEF DESCRIPTION OF DRAWINGS

FIG. 6 is a schematic cross-sectional view of one embodiment of a mold for making a microneedle array article according to the present disclosure.

FIG. 7 is a block diagram of one embodiment of a method of registering the location of at least one microneedle according to the present disclosure.

FIG. 8 is a block diagram of one embodiment of a method of making a microneedle article with a channel passing through at least one microneedle.

Figure 1A:
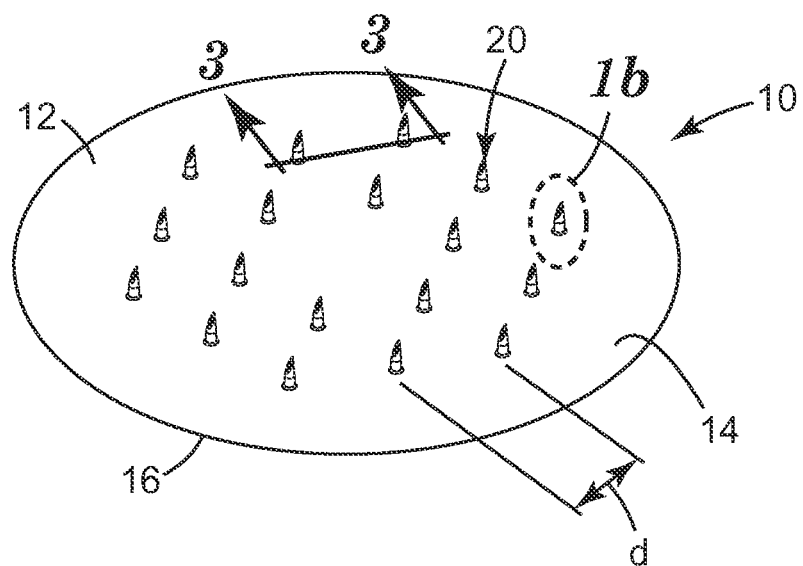
FIG. 1A is a perspective view of a first side of one embodiment of a microneedle array article according to the present disclosure.

While the above-identified drawing figures set forth several embodiments of the disclosure, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale.

DETAILED DESCRIPTION

The present disclosure generally relates to articles comprising microneedles and methods of making the articles. In one aspect, the present disclosure particularly provides a method of making an article comprising hollow microneedles. Advantageously, the process of the present disclosure may offer the ability to reproduce the mold shape in the resulting molded article reliably, to produce microneedles of a consistent height, to produce microneedles with a microscopic tip dimension (e.g., less than about 20 microns), and to produce hollow microneedle arrays in an economical fashion. Even further advantageously, the method can be used to make hollow microneedles having a particularly high aspect ratio (e.g., greater that 2:1 and up to about 5:1).

In another aspect, the present disclosure particularly provides articles comprising molded microneedles, the microneedles having first and second cavities that result in a thinned region in the body of the microneedle. The thinned region can be exploited to facilitate obtaining an image the cavities, which may simultaneously or subsequently be used to register the location of the microneedle on the article. Advantageously, imaging the cavities can be utilized to load a composition into one or more of the cavities and/or it may be utilized to guide a process of producing hollow microneedles from the microneedles comprising the first and second cavities.

In another aspect, the present disclosure particularly provides economical and highly-reproducible methods of using a laser to produce an article having hollow microneedles. Advantageously, the laser can be used with a mask element to form hollow channels simultaneously in a plurality of microneedles including, for example, high-aspect ratio microneedles.

In the present application, the resulting molded article can be used as a therapeutic device to deliver pharmaceutical compositions, after creating the channel that extends through each microneedle, is referred to as a hollow microneedle array. The hollow microneedle array is referred to in its use as a therapeutic device. However, the present disclosure should not be unduly limited to hollow microneedle arrays. Other microstructure articles are contemplated following the methods and procedures of the present disclosure, such as, for example, cylindrical posts, microelectronic devices, electrical connectors, medical microfluidic devices, fuel atomizers, and optoelectronic devices.

The present disclosure relates to the production of microneedles, and more specifically hollow microneedles. An ablation process (e.g., laser drilling) is used to create an open channel through the microneedles. To increase the probability of successfully creating the channel in microneedles made from a polymeric material, design features are added to minimize the amount of polymeric material that must be removed to create the channel. Advantageously, this improvement also lowers the cycle time to complete the formation of each channel.

FIG. 1A depicts a perspective view of a first side 14 of one embodiment of an article 10 comprising a plurality of microneedles 20. The article 10 comprises a substrate 12 having a plurality of microneedles 20 arrayed thereon. In the illustrated embodiment of FIG. 1A, the article comprises an array of eighteen microneedles. However, other arrangements and numbers of microneedles 20 are contemplated.

The microneedles 20 are spaced apart. In any embodiment, the distance "d" between adjacent microneedles 20 can be about 2 mm. In any embodiment, the substrate 12 can be disk-shaped, as shown in FIG. 1A, and can have an area of about 1.27 $cm^2$. In any embodiment, the microneedles 20 can be spread out over an area of about 1.42 $cm^2$, as measured using the perimeter of the outermost rows of microneedles 20. This configuration gives a microneedle density of about 13 microneedles/$cm^2$.

Figure 1B:
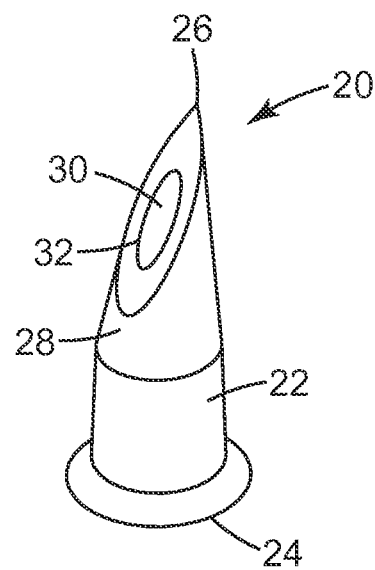
FIG. 1B is a detail view of one microneedle of the microneedle array article of FIG. 1A.

FIG. 1B shows a detail view of one of the microneedles 20 of the article 10 of FIG. 1A. Each microneedle 20 has a body 22 extending from a base 24 to a tip 26. The body 22 can have a height of approximately 500 μm, for example. A first cavity 30 extends into the microneedle 20 proximate the tip 26. Each first cavity 30 has a first opening 32 on a sloping side-wall 28 of the microneedle 20, similar to a hypodermic needle, and a first terminus (not shown). The configuration of the first opening 32 positioned on a sloping sidewall 28 helps prevent blockage by tissue upon insertion of the microneedle 20. The first cavity 30 may have an average diameter of at least about 10 μm.

Generally, an article 10 comprising a microneedle array includes a plurality of microneedles 20. FIG. 1 shows a microneedle array article 10 that includes eighteen microneedles 20. The body 22 of each microneedle 20 has a height h, which is the length from the tip 26 of the microneedle 20 to the microneedle base 24. Either the height of a single microneedle 20 or the average height of all microneedles on the microneedle array can be referred to as the height of the microneedle. In some embodiments, each microneedle of the plurality of microneedles (or the average of all of the plurality of microneedles) has a height of about 100 to about 3000 micrometers, about 100 to about 1500 micrometers, about 100 to about 1200 micrometers, or about 100 to about 1000 micrometers.

Figure 12:
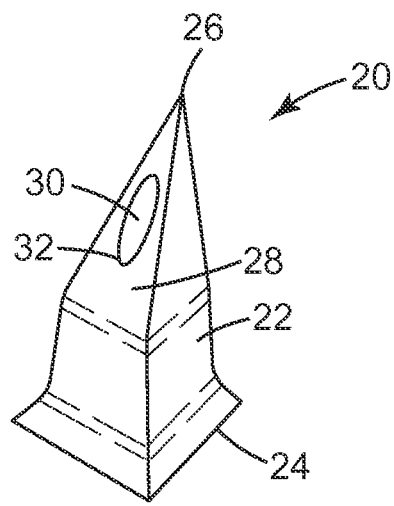
FIG. 12 is a detail view of an alternative embodiment of a microneedle comprising a first cavity according to the present disclosure.

The microneedles 20 depicted in FIG. 1 have a tapered cone shape. However, the microneedles may have a variety of alternative shapes, as described herein. FIG. 12 shows a detail view of one embodiment of a microneedle of the present disclosure having an alternative shape. In this embodiment, the microneedle 20 has a tapered square pyramidal shape. According to the present disclosure, the microneedle 20 has a body 22 extending from a base 24 to a tip 26. The body 22 further comprises a tapered wall 28 with a first cavity 30 extending into the body 22 from a first opening 32.

In some embodiments, each of the plurality of microneedles (or the average of all of the plurality of microneedles) has a height of about 200 to about 1200 micrometers, about 200 to about 1000 micrometers, about 200 to about 750 micrometers, or about 200 to about 600 micrometers.

In some embodiments, each of the plurality of microneedles (or the average of all of the plurality of microneedles) has a height of about 250 to about 1500 micrometers, about 500 to about 1000 micrometers, or about 500 to about 750 micrometers.

In some embodiments, each of the plurality of microneedles (or the average of all of the plurality of microneedles) has a height of about 800 to about 1400 micrometers.

In some embodiments, each of the plurality of microneedles (or the average of all of the plurality of microneedles) has a height of about 500 micrometer.

In some embodiments, each of the plurality of microneedles (or the average of all of the plurality of microneedles) has a height of less than about 3000 micrometers. In other embodiments, each of the plurality of microneedles (or the average of all of the plurality of microneedles) has a height of less than about 1500 micrometers. In still other embodiments, each of the plurality of microneedles (or the average of all of the plurality of microneedles) has a height of less than about 1200 micrometers. In yet still other embodiments, each of the plurality of microneedles (or the average of all of the plurality of microneedles) has a height of less than about 1000 micrometers. In further embodiments, each of the plurality of microneedles (or the average of all of the plurality of microneedles) has a height of less than about 750 micrometers. In still further embodiments, each of the plurality of microneedles (or the average of all of the plurality of microneedles) has a height of less than about 600 micrometers.

In some embodiments, each of the plurality of microneedles (or the average of all of the plurality of microneedles) has a height of greater than about 100 micrometers. In other embodiments, each of the plurality of microneedles (or the average of all of the plurality of microneedles) has a height of greater than about 200 micrometers. In still other embodiments, each of the plurality of microneedles (or the average of all of the plurality of microneedles) has a height of greater than about 250 micrometers. In further embodiments, each of the plurality of microneedles (or the average of all of the plurality of microneedles) has a height of greater than about 500 micrometers. In still further embodiments, each of the plurality of microneedles (or the average of all of the plurality of microneedles) has a height of greater than about 800 micrometers.

In one aspect, the present disclosure provides an article with comprising a plurality of solid microneedles (i.e., the "solid" microneedles do not comprise a through-hole extending from the first side of the article through the body of the microneedle to the second side of the article). In any embodiment, each microneedle of the plurality of solid microneedles (or the average of all of the plurality of solid microneedles) has a height of about 100 to about 1500 micrometers, about 100 to about 1200 micrometers, about 200 to about 1000 micrometers, about 200 to about 750 micrometers, about 200 to about 600 micrometers, or about 500 micrometers.

In another aspect, the present disclosure provides an article comprising a plurality of hollow microneedles (i.e., the "hollow" microneedles comprise a through-hole extending from the first side of the article through the body of the microneedle to the second side of the article). In any embodiment, each microneedle of the plurality of hollow microneedles (or the average of all of the plurality of hollow microneedles) has a height of about 100 to about 3000 micrometers, about 800 to about 1400 micrometers, or about 500 micrometers.

In any embodiment, each microneedle of the plurality of hollow microneedles (or the average of all of the plurality of hollow microneedles) has a height of about 900 to about 1000 micrometers. In any embodiment, each microneedle of the plurality of hollow microneedles (or the average of all of the plurality of hollow microneedles) has a height of about 900 to about 950 micrometers. In any embodiment, each microneedle of the plurality of hollow microneedles (or the average of all of the plurality of hollow microneedles) has a height of about 900 micrometers.

A single microneedle or the plurality of microneedles in a microneedle array article can also be characterized by its aspect ratio. The aspect ratio of a microneedle is the ratio of the height of the microneedle, h to the width (at the base of the microneedle), w (as seen in FIG. 1B). The aspect ratio can be presented as h:w. In any embodiment, each microneedle of the plurality of microneedles (or the average of all the plurality of microneedles) has (have) an aspect ratio in the range of 2:1 to 5:1. In any embodiment, each of the plurality of microneedles (or the average of all of the plurality of microneedles) has (have) an aspect ratio of at least 3:1. In any embodiment, each of the plurality of microneedles (or the average of all of the plurality of microneedles) has (have) an aspect ratio of at least 3:1. In any embodiment, each of the plurality of microneedles (or the average of all of the plurality of microneedles) has (have) an aspect ratio of at least 4:1. In any embodiment, each of the plurality of microneedles (or the average of all of the plurality of microneedles) has (have) an aspect ratio of at least 5:1. In any embodiment, each of the plurality of microneedles (or the average of all of the plurality of microneedles) has (have) an aspect ratio between 3:1 and 5:1, inclusive. In any embodiment, each of the plurality of microneedles (or the average of all of the plurality of microneedles) has (have) an aspect ratio between 3:1 and 4:1, inclusive. In any embodiment, each of the plurality of microneedles (or the average of all of the plurality of microneedles) has (have) an aspect ratio between 3:1 and 5:1, inclusive. In any embodiment, each of the plurality of microneedles (or the average of all of the plurality of microneedles) has (have) an aspect ratio between 4:1 and 5:1, inclusive.

In any embodiment, an array of microneedles contains about 100 to about 1500 microneedles per $cm^2$ of the array of microneedles.

In any embodiment, an array of microneedles (e.g., solid microneedles or hollow microneedles) contains about 3 to about 30 microneedles per array. In any embodiment, an array of microneedles (e.g., solid microneedles or hollow microneedles) contains about 10 to about 30 microneedles per array. In any embodiment, an array of microneedles (e.g., solid microneedles or hollow microneedles) contains about 3 to about 20 microneedles per array. In any embodiment, an array of microneedles (e.g., solid microneedles or hollow microneedles) contains about 13 to about 20 microneedles per array. In any embodiment, an array of microneedles (e.g., solid microneedles or hollow microneedles) contains about 8 to about 18 microneedles per array. In any embodiment, an array of microneedles (e.g., solid microneedles or hollow microneedles) contains about 18 microneedles per array. In any embodiment, an array of microneedles (e.g., solid microneedles or hollow microneedles) contains about 100 to about 1500 microneedles per array. In any embodiment, an array of microneedles (e.g., solid microneedles or hollow microneedles) contains about 200 to about 500 solid microneedles per array. In any embodiment, an array of microneedles (e.g., solid microneedles or hollow microneedles) contains about 300 to about 400 microneedles per array.

In any embodiment, each of the plurality of microneedles (or the average of all of the plurality of microneedles) in a microneedle array can penetrate into the skin to a depth of about 50 to about 1500 micrometers, about 50 to about 400 micrometers, or about 50 to about 250 micrometers. In any embodiment, each of the plurality of microneedles (or the average of all of the plurality of microneedles) in a microneedle array can penetrate into the skin to a depth of about 100 to about 400 micrometers, or about 100 to about 300 micrometers. In any embodiment, each of the plurality of microneedles (or the average of all of the plurality of microneedles) in a microneedle array can penetrate into the skin to a depth of about 150 to about 1500 micrometers, or about 800 to about 1500 micrometers. In any embodiment, each of the plurality of microneedles (or the average of all of the plurality of microneedles) in a microneedle array can penetrate into the skin to a depth of about 400 to about 800 micrometers. For all of the above embodiments, it will be appreciated that the depth of penetration of each of the plurality of microneedles (or the average of all of the plurality of microneedles) in a microneedle array may not be the full length of the microneedles themselves.

In any embodiment, the surface area of the substrate 12 covered with microneedles is about 0.1 cm$^2$ to about 20 cm$^2$. In some of these embodiments, the surface area of the substrate 12 covered with microneedles is about 0.5 cm$^2$ to about 5 cm$^2$. In some other of these embodiments, the surface area of the substrate 12 covered with microneedles is about 1 cm$^2$ to about 3 cm$^2$. In still other of these embodiments, the surface area of the substrate 12 covered with microneedles is about 1 cm$^2$ to about 2 cm$^2$.

In any embodiment (not shown), the microneedles can be disposed over substantially the entire surface of the article. In other embodiments (not shown), a portion of the substrate is not provided with microneedles (that is, that is a portion of the substrate is non-structured). In some of these embodiments, the non-structured surface has an area of more than about 1 percent and less than about 75 percent of the total area of the device surface that faces the skin surface. In another of these embodiments, the non-structured surface has an area of more than about 0.65 cm$^2$ (0.10 square inch) to less than about 6.5 cm$^2$ (1 square inch).

For hollow microneedles, a hollow channel or bore extends through the substrate and microneedle. In some embodiments, the bore exits at a channel opening at or near the tip of the hollow microneedle. The channel preferably exits at an opening near the tip of the hollow microneedle. Most preferably, the channel or bore continues along a central axis of the microneedle, but exits similar to a hypodermic needle on a sloping side-wall of the microneedle to help prevent blockage of the channel by tissue upon insertion. In any embodiment, the diameter of the channel bore is about 10 to about 200 micrometers. In some embodiments, the diameter of the channel bore is about 10 to about 150 micrometers. In other embodiments, the diameter of the channel bore is about 30 to about 60 micrometers.

In any embodiment of hollow microneedles, the average cross-sectional area of the channel bore is about 75 to about 32,000 μm$^2$. In some embodiments of hollow microneedles, the average cross-sectional area of the channel bore is about 75 to about 18,000 μm$^2$. In other embodiments of hollow microneedles, the average cross-sectional area of the channel bore is about 700 to about 3,000 μm$^2$.

In any embodiment of microneedle arrays (e.g., solid microneedle array or hollow microneedle array), the average spacing between adjacent microneedles (as measured from microneedle tip to microneedle tip) is between about 0.7 mm and about 20 mm. In embodiment of microneedle arrays (e.g., solid microneedle array or hollow microneedle array), the average spacing between adjacent microneedles is between about 0.7 mm and about 10 mm. In any embodiment of microneedle arrays (e.g., solid microneedle array or hollow microneedle array), the average spacing between adjacent microneedles is between about 2 mm and about 20 mm. In any embodiment of microneedle arrays (e.g., solid microneedle array or hollow microneedle array), the average spacing between adjacent microneedles is between about 2 mm and about 10 mm. In a preferred embodiment of microneedle arrays (e.g., solid microneedle array or hollow microneedle array), the average spacing between adjacent microneedles is about 2 mm.

In any embodiment of microneedle arrays (e.g., solid microneedle array or hollow microneedle array), the average spacing between adjacent microneedles (as measured from microneedle tip to microneedle tip) is greater than about 0.7 mm. In any embodiment of hollow microneedle arrays (e.g., solid microneedle array or hollow microneedle array), the average spacing between adjacent microneedles is greater than about 2 mm.

In any embodiment of microneedle arrays (e.g., solid microneedle array or hollow microneedle array), the average spacing between adjacent microneedles is less than about 20 mm. In any embodiments of microneedle arrays (e.g., solid microneedle array or hollow microneedle array), the average spacing between adjacent microneedles is less than about 10 mm.

In any embodiment of microneedle arrays (e.g., solid microneedle array or hollow microneedle array), the average spacing between adjacent microneedles (as measured from microneedle tip to microneedle tip) is between about 200 micrometers and about 2000 micrometers. In any embodiments of microneedle arrays (e.g., solid microneedle array or hollow microneedle array), the average spacing between adjacent microneedles is between about 200 micrometers and about 600 micrometers. In any embodiment of microneedle arrays (e.g., solid microneedle array or hollow microneedle array), the average spacing between adjacent microneedles is between about 200 micrometers and about 300 micrometers. In any embodiment of microneedle arrays (e.g., solid microneedle array or hollow microneedle array), the average spacing between adjacent microneedles is between about 500 micrometers and about 600 micrometers.

In any embodiment of microneedle arrays (e.g., solid microneedle array or hollow microneedle array), the average spacing between adjacent microneedles (as measured from microneedle tip to microneedle tip) is greater than about 200 micrometers. In any embodiments of microneedle arrays (e.g., solid microneedle array or hollow microneedle array), the average spacing between adjacent microneedles is greater than about 500 micrometers.

In any embodiment of microneedle arrays (e.g., solid microneedle array or hollow microneedle array), the average spacing between adjacent microneedles is less than about 2000 micrometers. In any embodiment of microneedle arrays (e.g., solid microneedle array or hollow microneedle array), the average spacing between adjacent microneedles is less than about 1000 micrometers. In any embodiment of microneedle arrays (e.g., solid microneedle array or hollow microneedle array), the average spacing between adjacent microneedles is less than about 600 micrometers. In any embodiment of microneedle arrays (e.g., solid microneedle array or hollow microneedle array), the average spacing between adjacent microneedles is less than about 300 micrometers.

Figure 2A:
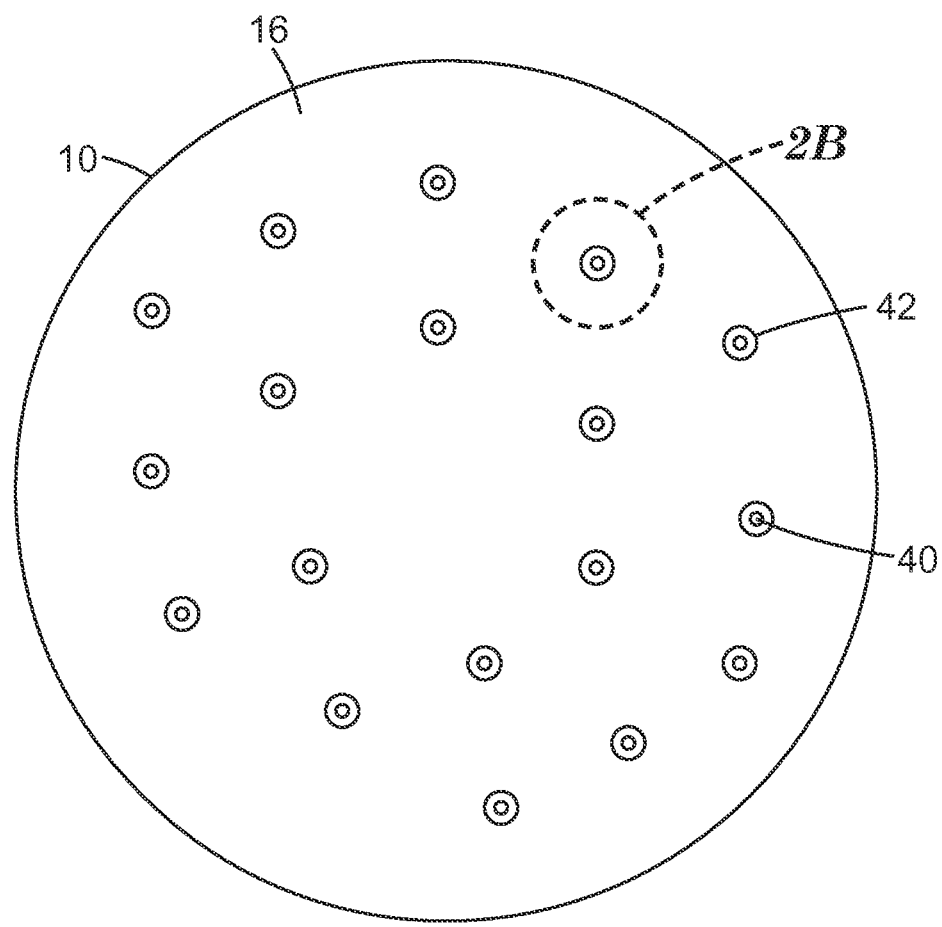
FIG. 2A is a plan view of a second side of the microneedle array article of FIG. 1A, showing a plurality of one embodiment of a second cavity according to the present disclosure.
Figure 2B:
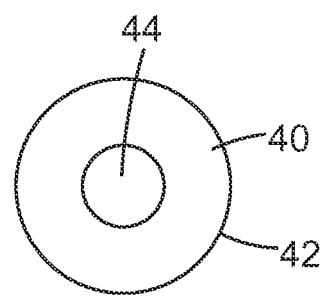
FIG. 2B is a detail view of one second cavity of the article of FIG. 2A.

Referring back to the drawings, FIG. 2A shows a plan view of the second side 16 of the article 10 of FIG. 1A. Aligned, as described herein, with each of the microneedles 20 on the first side 14 of the article 10 is a corresponding second cavity 40. FIG. 2B shows a detail view of one of the second cavities 40 of FIG. 2A. Each second cavity 40 comprises a second opening 42 and a second terminus 46.

The article 10 can be made, for example, by injection molding of a polymer (e.g., medical grade polycarbonate, liquid crystal polymers), followed by laser drilling to form the channel of the microneedle 20 as described herein.

The article 10 can be formed with a rim structure (not shown) that can be used for attaching the substrate 12 to a backing member (not shown) in order to secure the article to a patient's skin during use. Such rim structures and backings are described in U.S. Patent Application Publication No. 2011/0213335, which is incorporated herein by reference in its entirety.

The microneedle article 10 is typically applied to the skin using an external applicator (not shown). The applicator can be designed, e.g., using a spring mechanism, to achieve a desired velocity so the microneedles will penetrate into the skin rather than merely deforming the skin. Once applied, the backing member (not shown) secures the microneedle device against the skin. Various applicator devices are disclosed in, for example, WO2005/123173, WO2006/055802, WO2006/055771, WO2006/108185, WO2007/002521, and WO2007/002522, which are all incorporated herein by reference in their entirety.

Figure 3:
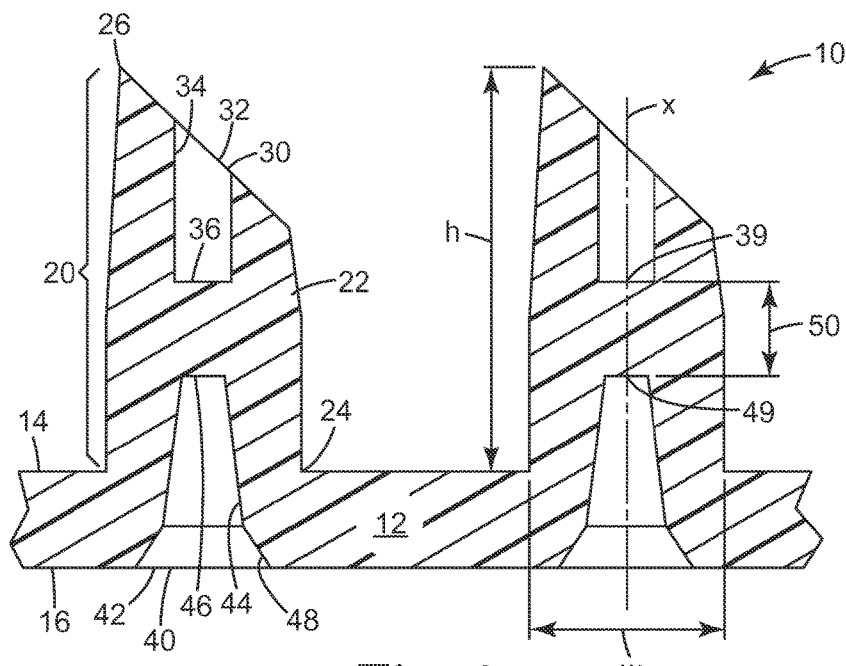
FIG. 3 is cross-sectional view of a portion of the microneedle array article of FIG. 1A.

FIG. 3 shows a cross-sectional view of a portion of the substrate 12 of the article 10 of FIG. 1A. The microneedles 20 extend from the first side 14 of the substrate 12. Each microneedle 20 comprises a body 22 with a base 24, a tip 26, and a first cavity 30 extending into the body 22 proximate the tip 26. Each microneedle 20 further comprises a central axis "x". The first cavity 30 comprises a first opening 32, at least one side-wall 34, and a first terminus 36. Although not required, in any embodiment, the first cavity 30 may be substantially aligned with, and optionally centered along, the central axis x of the microneedle 20.

Also shown in FIG. 3 is a second cavity 40. The second cavity 40 comprises a second opening 42, at least one side-wall 44, and a second terminus 46. Optionally, the second cavity 40 further may comprise a chamfer 48 proximate the second opening 42 as illustrate in FIG. 3 and/or a chamfer (not shown) proximate the second terminus 46. Advantageously, the chamfer 48 can reduce the amount of material required to make the article 10. The second cavity 40 extends through the substrate 12 into the body 22 of the microneedle 20. Disposed between the first cavity 30 and the second cavity 40 in the body 22 of the microneedle 20 is a thinned region 50. The thinned region 50 can be used to map the location of a microneedle 20, as described herein. In the formation of hollow microneedles as described herein, a through-hole (not shown) is formed by removing (e.g., by laser ablation) at least a portion of the material in the thinned region and thereby placing the first cavity 30 in fluidic communication with the second cavity 40.

Microneedle articles of the present disclosure are produced using a molding process. In any embodiment, either the first terminus or the second terminus may be molded to include an optically-distinguishable feature (e.g., a slightly raised feature, not shown), such as a letter, a line, a circle, a cross-hair pattern or the like.

Although not required, in any embodiment, the second cavity 40 may be substantially aligned with, and optionally centered along, the central axis x of the microneedle 20, as shown in FIG. 3. This configuration (i.e., alignment of the first cavity 30 and second cavity 40 along a common axis (e.g., the central axis of the microneedle 20) provides a straight-line path (e.g., central axis x) passing through the substrate 12. Preferably, the straight-line path passes through the substrate 12 only once. For example, the straight-line path can enter the substrate 12 at a first point 39 in the first cavity 30 and exit the substrate 12 at a second point 49 in the second cavity 40. A person having ordinary skill in the art will recognize a variety of other possible first cavity entrance points and second cavity exit points for a straight line passing through the thinned region 50 can have.

Having a straight-line path that passes only once through the substrate, preferably from a point located in the first cavity to a point located in the second cavity or from a point located in the second cavity to a point located in the first cavity, means you can use a controlled process (e.g., a laser ablation process) that will only affect (e.g., remove) the substrate material that is positioned along the straight-line path between the first cavity and the second cavity. In preferred embodiments, it is desirable to direct the through-hole along a path that does not intersect the tip of a microneedle because the tip of the microneedle could be damaged or deformed (by heat generated by a laser ablation process, for example), thereby adversely affecting the performance of the microneedle.

Figure 4:
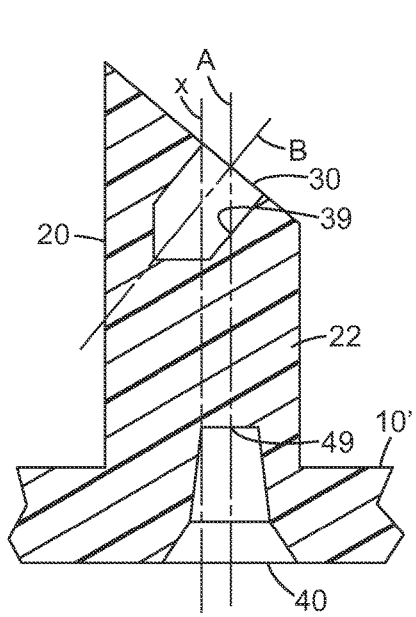
FIG. 4 is a cross-sectional view of one embodiment of a microneedle having first and second cavities that extend into the microneedle at nonparallel, angles.

FIG. 4 shows a cross-sectional view of a portion of an alternative embodiment of an article 10' comprising a microneedle 20 with first and second cavities according the present disclosure. In this embodiment, the article 10' comprises a microneedle 20 with a body 22 having a first cavity 30 and a second cavity 40 extending therein. The microneedle 20 has a central axis X. The first cavity 30 comprises a first cavity longitudinal axis B that intersects the microneedle central axis x, but is neither parallel to nor substantially aligned along the central axis X of the microneedle 20. In addition, the second cavity 40 comprises a second cavity longitudinal axis A that is parallel to, but not substantially aligned along, the microneedle central axis X. However, with this configuration, there exists at least one straight-line path (e.g., coincident with second cavity longitudinal axis A) that enters the substrate 12 at a first point 39 in the first cavity 30, exits the substrate 12 at a second point 49 in the second cavity 40, and passes through the substrate material (e.g., passes through the substrate material only once). Thus, a microneedle configuration such as the one illustrated in FIG. 4 can be used to make an article with hollow microneedles according to the present disclosure.

Figure 5:
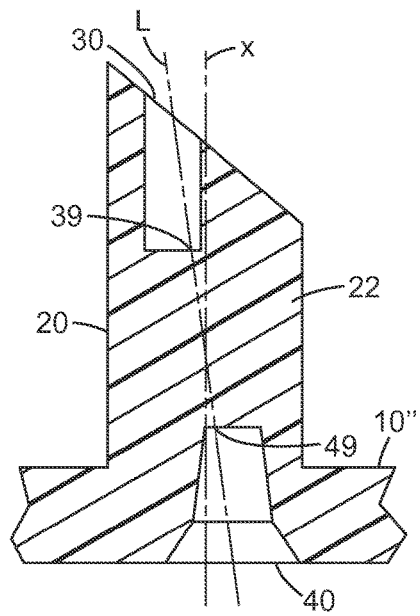
FIG. 5 is a cross-sectional view of one embodiment of a microneedle having first and second cavities that extend through the microneedle at parallel angles and showing a straight line that passes only once through the substrate after entering the substrate at a first point in the second cavity and exiting the substrate at a second point in the first cavity.

FIG. 5 shows a cross-sectional view of a portion of another alternative embodiment of an article 10'' comprising a microneedle 20 with first and second cavities according the present disclosure. In this embodiment, the article 10'' comprises a microneedle 20 with a body 22 having a first cavity 30 and a second cavity 40 extending therein. The microneedle 20 has a central axis X. Both the first cavity 30 and the second cavity 40 extend into the body 22 of the microneedle 20 in a direction parallel to, but not substantially aligned along, the microneedle central axis X. However, with this configuration, there exists at least one straight-line path (e.g., line L) that enters the substrate 12 at a first point 39 in the first cavity 30, exits the substrate 12 at a second point 49 in the second cavity 40, and passes through the substrate material only once. Thus, a microneedle configuration such as the one illustrated in FIG. 5 can be used to make an article with hollow microneedles according to the present disclosure.

Microneedle array articles (e.g., including articles comprising hollow microneedles) that are made according to the present disclosure can have a variety of configurations and features, such as those described in the following patents and patent applications, the disclosures of which are incorporated herein by reference in their entirety. One embodiment for the microneedle array articles includes the structures disclosed in U.S. patent application Publication No. 2005/0261631 (Clarke et al.), which describes microneedles having a truncated tapered shape and a controlled aspect ratio. Another embodiment for the microneedle arrays includes the structures disclosed in U.S. Pat. No. 6,091,975 (Daddona et al.), which describes blade-like microprotrusions for piercing the skin. Still another embodiment for the microneedle arrays includes the structures disclosed in U.S. Pat. No. 6,312,612 (Sherman et al.), which describes tapered structures having a hollow central channel. Yet still another embodiment for the microneedle array articles includes the structures disclosed in U.S. Pat. No. 6,379,324 (Garstein et al.), which describes hollow microneedles having at least one longitudinal blade at the top surface of the tip of the microneedle. A further embodiment for the microneedle array articles includes the structures disclosed in U.S. patent application Publication Nos. US2012/0123387 (Gonzalez et al.) and US2011/0213335 (Burton et al.), which both describe hollow microneedles. A still further embodiment for the microneedle array articles includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of microneedles that can be employed in the microneedle arrays of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

Articles comprising microneedles with first and second cavities according to the present disclosure can be made, for example, by injection molding processes that are known in the art. In some embodiments, the microneedle material can be (or include) a metal or a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

The microneedle arrays of the present disclosure can be manufactured in any suitable way such as by injection molding, compression molding, metal injection molding, stamping, or extrusion. In any embodiment, hollow microneedle arrays can be made by injection molding of a polymer such as medical grade polycarbonate or LCP, followed by laser drilling to form the channels of the microneedles. Nonlimiting examples of molding processes for molding polymeric materials into the solid microneedle articles of the present disclosure can be found in U.S. Pat. No. 8,088,321 (Ferguson et al.) and U.S. patent application Publication Nos. 2012/0258284 (Rendon) and 2012/0041337 (Ferguson et al.), each of which is incorporated herein by reference in its entirety.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In any embodiment, the microneedles can be made from (or include) a combination of two or more of any of the above mentioned materials. For example, the tip of a microneedle may be a dissolvable material, while the remainder of the microneedle is a medical grade polymeric material.

A microneedle or the plurality of microneedles in a microneedle array article of the present disclosure can have a variety of shapes that are capable of piercing the stratum corneum. In some of the embodiments, one or more of the plurality of microneedles can have a square pyramidal shape, triangular pyramidal shape, stepped pyramidal shape, conical shape, microblade shape, or the shape of a hypodermic needle. In any embodiment, one or more of the plurality of microneedles can have a square pyramidal shape. In any embodiment, one or more of the plurality of microneedles can have a triangular pyramidal shape. In any embodiment, one or more of the plurality of microneedles can have a stepped pyramidal shape. In any embodiment, one or more of the plurality of microneedles can have a conical shape. In any embodiment, one or more of the plurality of microneedles can have a microblade shape. In any embodiment, one or more of the plurality of microneedles can have the shape of a hypodermic needle. In any embodiment, a microneedle array article may comprise an array of microneedles having a combination of any two or more of the foregoing microneedle shapes. The shape of any microneedle in the microneedle array article can be symmetric or asymmetric. The shape of any microneedle in the microneedle array article can be truncated (for example, the plurality of microneedles can have a truncated pyramid shape or truncated cone shape). In a preferred embodiment, each microneedle of the plurality of microneedles in a microneedle array article has a square pyramidal shape.

In any embodiment, each microneedle of the plurality of microneedles in a microneedle array article is solid microneedles (that is, the microneedles do not comprise a through-hole). In any embodiment, each microneedle of the plurality of solid microneedles in a solid microneedle array article can have a square pyramidal shape, triangular pyramidal shape, stepped pyramidal shape, conical shape, or microblade shape. In a preferred embodiment, each microneedle of the plurality of solid microneedles in a solid microneedle array article has a square pyramidal shape.

In some embodiments, each microneedle of the plurality of microneedles in a microneedle array is a hollow microneedle (that is, the microneedle contains a hollow bore through the microneedle). The hollow bore can be from the base of the microneedle to the tip of the microneedle or the bore can be from the base of the microneedle to a position offset from the tip of the microneedle. In any embodiment, one or more of the plurality of hollow microneedles in a hollow microneedle array can have a conical shape, cylindrical shape, square pyramidal shape, triangular pyramidal shape, or the shape of a hypodermic needle.

In any embodiment, one or more microneedle of the plurality of hollow microneedles in a hollow microneedle array article can have a conical shape. In any embodiment, one or more microneedle of the plurality of hollow microneedles in a hollow microneedle array article can have a cylindrical shape. In any embodiment, one or more microneedle of the plurality of hollow microneedles in a hollow microneedle array article can have a square pyramidal shape. In any embodiment, one or more microneedle of the plurality of hollow microneedles in a hollow microneedle array article can have a triangular pyramidal shape. In any embodiment, one or more microneedle of the plurality of hollow microneedles in a hollow microneedle array article can have the shape of a hypodermic needle. In a preferred embodiment, each microneedle of the plurality of hollow microneedles in a hollow microneedle array article has the shape of a conventional hypodermic needle.

The microneedle array articles of the present disclosure can be manufactured by injection molding of a polymer such as medical grade polycarbonate or LCP. Typically, these processes use molds to form the substrate with the microneedles extending therefrom.

FIG. 6 depicts a side view of an exemplary mold assembly 600 for forming an article comprising microneedles according to the present disclosure. The mold assembly comprises a first mold half 70 in contact with a second mold half 65. Projections 82 extend outward from the first mold half 70 to form the first cavity in the molded microneedles (see first cavity 30 of FIG. 3). Projections 80 extend outward from the second mold half 65 to form the second cavity in the molded microneedles (see second cavity 40 of FIG. 3). Molten polymeric material fills the area between the planar surfaces of the first mold surface and the second mold surface. Because of the space between the neck of the projections and the cavity surface, molten polymeric material will fill in around projections 80 and 82, respectively, into the apex of cavity 60. The length 85 between the planar surfaces of the first mold surface and the second mold surface may define the thickness of the substrate of the resulting molded article. In any embodiment, the substrate is about 0.5 mm to about 1.0 mm thick. A person having ordinary skill in the art will appreciate substrates having other thicknesses may be useful for certain applications. After the molten polymeric material is cooled and hardened, the mold halves are separated and the resulting molded article (e.g., the microneedle array article) is removed.

In any embodiment of the present disclosure, the first and/or second mold half comprises mold materials of at least one of: steel, steel alloys, aluminum, aluminum alloys, nickel, nickel alloys, copper, copper alloys, beryllium copper, beryllium copper alloys, or combinations thereof.

The projections may be machined using, for example, milling, cutting, grinding, chemically etching, electrode discharge machining, electrochemical etching, laser ablation, focused ion beam machining, or combinations thereof. Milling tools can be used to cut the projections including, for example, square end or round end milling machine cutters, a suitable tapered cutting or grinding wheel, or the like.

The first mold half and second mold half are contacted together via physical means, using for example, side and/or parting taper locks for alignment of the mold halves. Active alignment, involving mechanical means, is used to register (i.e., each projection is aligned within their respective cavity) the mold halves. In one embodiment, the registering is less than 10, 7, 5, 4, 2, or even 1 µm.

Various molding techniques, as are known in the art, including for example: compression molding, thermal embossing, thermoplastic (TP) or thermoset (TS) injection molding (IM), injection-compression molding (ICM), powder injection molding (PIM), liquid injection molding (LIM), reactive injection molding (RIM), ceramic injection molding (CIM), metal injection molding (MIM) and cast extrusion; may be envisioned using the mold halves as described herein.

In one embodiment, it may be desirable to add a compressive force or coining to the molten polymeric material in the first mold half in order to assist in filling the cavities, such as described in U.S. patent application Publication No. 2008/0088066 AI (Ferguson et al.). Additional details regarding injection-compression molding may be found in U.S. Pat. No. 4,489,033 (Uda et al.), U.S. Pat. No. 4,515,543 (Hamner), and U.S. Pat. No. 6,248,281 (Abe et al.).

The resulting molded article (e.g., microneedle array articles) may be manufactured from a variety of materials. Material selection may be based on a variety of factors including the ability of the material to accurately reproduce the desired pattern; the strength and toughness of the material when formed into the hollow microneedle array; the compatibility of the material with, for example, human or animal skin; the compatibility of the materials with any fluids that will be expected to contact the hollow microneedle array, etc.

Suitable polymeric materials for the hollow microneedle array articles of the present disclosure may include, for example: polycarbonate, cyclic olefin copolymer, liquid crystal polymer, polyacrylate, acrylate copolymer, polystyrene, polypropylene, polyethylene, polyester, polyamide, polyamide imide, polyetheretherketone, polyetherimide, polybutylene terephthalate, polyphenyl sulfides, acetals, polyethylene terephthalates polyvinyl chloride, polymethylmethacrylate, acrylonitrile-butadiene styrene, or combinations thereof.

It may be preferred that the polymeric materials have one or more of the following properties: high tensile elongation at break, high impact strength, and high meltflow index. In one aspect, the melt-flow index as measured by ASTM D1238 (conditions: 300° C., 1.2 kg weight) is greater than about 5 g/10 minutes. The melt-flow index as measured by ASTM D1238 (conditions: 300° C., 1.2 kg weight) is greater than about 10 g/10 minutes, or even between about 20 g/10 minutes and 30 g/l 0 minutes. In one aspect, the tensile elongation at break as measured by ASTM D638 (2.0 in/minute) is greater than about 100%. In one aspect, the impact strength as measured by ASTM D256, "Notched Izod", (73° F., 23° C.) is greater than about 5 ft-lb/inches (265 J/m).

Depending on the molding technique used, either the mold assembly is heated to melt a sheet of polymeric material or molten material is injected into the mold assembly. The heating of the first and/or second mold halves above the softening temperature of the polymeric material allows the polymeric material to substantially fill the cavities and micrometer features in the mold assembly. It is important that the polymeric material not be allowed to substantially cool before filling the micrometer features, since it can "skin over" or solidify in the cavities prior to complete filling and block further flow of molten material.

The "softening temperature" refers to the temperature at which a polymeric material will soften and deform when subject to ordinary forces, such as those encountered during detachment of a resulting molded article from a mold half. This may be conveniently measured by the Vicat softening temperature, which measures the temperature at which a flat-ended needle penetrates into a test sample (under conditions, for example, of a 50 N loading on the needle and a rate of temperature increase of 120° C./h as described in ASTM D1525-00). For amorphous materials, the softening temperature will be governed by the glass transition of the material, and in some instances the glass transition temperature will be essentially equivalent to the Vicat softening temperature. The glass transition temperature may be measured by methods known to one skilled in the art, such as by differential scanning calorimetry using a typical scanning rate of 10° C./min.

One manner in which the resulting molded article (e.g., hollow microneedle) of the present disclosure may be characterized is by height. The height of the hollow microneedle may be measured from the relatively planar resulting molded article support base. In one embodiment, the height of the hollow microneedle is 3000 µm or less, 2500 µm or less, 2000 µm or less, 1500 µm or less, 1000 µm or less, 750 µm or less, 500 µm or less, 300 µm or less, or even 100 µm or less, as measured from the base of the hollow microneedle to the apex. In one embodiment, the height of the hollow microneedle is greater than 90%, or even greater than about 95% of the corresponding cavity length in the first mold half. The hollow microneedles may deform slightly or elongate upon ejection from the mold assembly. This condition is most pronounced if the molded material has not cooled below its softening temperature, but may still occur even after the material is cooled below its softening temperature. In one embodiment, that the height of the hollow microneedles is less than about 115% or even less than about 105% of the cavity length in the first mold half. In one embodiment, the height of the hollow microneedle is substantially the same (e.g., 95% to 105%) as the corresponding cavity length in the first mold half.

The general shape of the microneedles of the present disclosure is tapered. For example, the hollow microneedles have a larger base at the resulting molded article support base and extend away from the resulting molded article support base, tapering to an apex. In one embodiment the shape of the hollow microneedle is pyramidal. In another embodiment, the shape of the hollow microneedle is generally conical.

After the article comprising solid microneedles has been formed, one or more of the microneedles optionally can be processed to produce a through-hole, bore, or channel, resulting in the formation of one or more hollow microneedles in the article. In order to accomplish this, the location of each microneedle in the article must be precisely determined so that the process of making the through-hole can be directed to the appropriate location of the substrate. Thus, in one aspect, the present disclosure provides a method of determining the location of a microneedle.

FIG. 7 shows one embodiment of a method 100 of determining the location of a microneedle according to the present disclosure. The method 100 comprises the step 121 of providing an article comprising a molded substrate having a plurality of microneedles extending therefrom, each microneedle having a first cavity extending into the body of the microneedle from a first side of the substrate and a second cavity extending into the body of the microneedle from a second side of the substrate, as described herein. The method 100 further comprises the step 123 of affixing the article. The article can be affixed, for example, to an apparatus that is configured to orient the substrate on a predefined plane (e.g., via a 2-axis X-Y stage) or in a predefined space (e.g., via a 3-axis X-Y-Z stage) so that a specific point on or in the article is disposed at a defined location within the predefined plane or space. A nonlimiting example of an apparatus suitable for affixing the article is a 3-axis stage combined with a rotation stage, available from PI miCos GmbH (Eschbach, Germany).

After affixing the article, the method 100 comprises the step 125 of registering the location of at least one microneedle. Registering the location of the microneedle can comprise directing electromagnetic radiation toward the first or second side of the article. The electromagnetic radiation can comprise a relatively wide band of wavelengths (e.g., white light) or a relatively narrow band of wavelengths (e.g., blue light). The electromagnetic radiation may be in the ultraviolet wavelengths or visible wavelengths, or a combination thereof. The wavelength(s) used in the method should include at least one wavelength that is absorbed or scattered by the material used to form the substrate. Thus, a difference in the thickness of the substrate material at any location in the article (e.g., the thinned region of the microneedle) may be detectable by observing a difference in the amount of electromagnetic radiation transmitted through the substrate material (or reflected or scattered by the substrate material) at that location relative to the adjacent locations. The wavelength and intensity of the electromagnetic radiation should be selected so as to provide detectable contrast between relatively thicker portions of the substrate and relatively thinner portions of the substrate.

While directing electromagnetic radiation toward a side of the article, an image of article (i.e., an image of the side of the article opposite the source of electromagnetic radiation) is obtained. That is, if the electromagnetic radiation is directed toward the first side of the substrate, an image of the second side of the substrate is obtained. Conversely, if the electromagnetic radiation is directed toward the second side of the substrate, an image of the first side of the substrate is obtained. In any embodiment, the electromagnetic radiation may be directed toward a side (e.g., the first side) of the substrate and an image of the same side (i.e., the first side) can be obtained. The image can be obtained using a variety of imaging devices, the devices optionally being part of a vision system. A non-limiting example of a suitable imaging device is a CCD camera (model KS722UP) obtained from NET New Electronic Technology GmbH, Finning, Germany).

Figure 9:
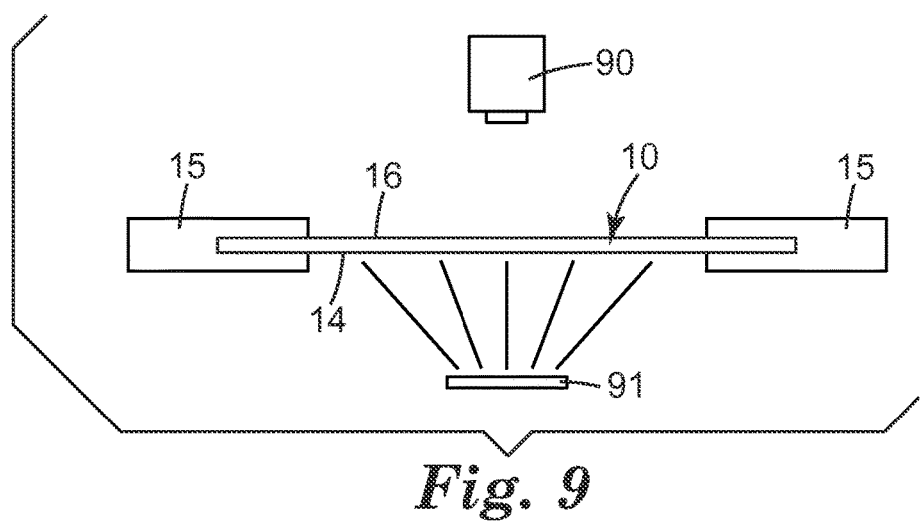
FIG. 9 is a schematic side view of one embodiment of a first subsystem for registering the location of a microneedle, the subsystem being part of a system for forming a hollow channel through the microneedle according to the present disclosure.

FIG. 9 shows a schematic side view of one embodiment of a system for imaging an article comprising microneedles, according to the present disclosure. The system comprises an apparatus 15 configured to hold an article 10 comprising a plurality of microneedles, each microneedle comprising a body having a first cavity and second cavity extending therein according to the present disclosure. The article 10 comprises a first side 14 having the plurality of microneedles (not shown) extending therefrom and a second side 16 opposite the first side. The apparatus 15 is configured to orient the substrate on a predefined plane or in a predefined space as described herein. The system further comprises a source 91 of electromagnetic radiation (e.g., a light), as described herein, facing the first side 14 of the article 10. The source 91 directs electromagnetic radiation (e.g., white light, visible wavelengths of light, ultraviolet light, near-infrared, infrared) toward the first side 14. Preferably, the electromagnetic radiation is substantially columnated. In some embodiments, the electromagnetic radiation can be delivered to the article 10 through a fiberoptic bundle (not shown). Facing the second side 16 of the article 10 is an imaging device 90 (e.g., a CCD camera). The imaging device 90 is configured to capture an image of the electromagnetic radiation transmitted through (and/or scattered by) the article 10. Typically, the imaging device 90 comprises and/or is operationally coupled to a microproccessor (e.g., a computer, not shown) configured to receive and analyze an image. In addition, the apparatus 15 may comprise and/or be operationally coupled to a microprocessor (e.g., a computer, not shown) that can controls the movement of the article 10 within a predefined plane or space.

The image is analyzed to identify locations of the substrate that have relatively higher contrast with other locations of the substrate (i.e., the regions are relatively highly-transmissible or relatively light-absorptive or light-scattering). In any embodiment, highly-transmissible locations correspond to the thinned regions (i.e., the relatively thin portions of the substrate material located between the first terminus of the first cavity and the second terminus of the second cavity (see FIG. 3)). A bit-map of the image is registered (e.g., by using a predefined reference point on the apparatus to which the article is affixed) with the predefined X-Y plane of the apparatus, thereby creating a spatial map of the location of each microneedle in the plurality of microneedles in the article. This spatial map can be used to direct a suitable process for creating through-holes in the microneedles. Alternatively, or additionally, the spatial map can be used to direct a process of precisely loading (e.g., via a robotic pipettor) a material onto the microneedles and/or into the first cavities of the microneedles.

An article comprising an array of microneedles can comprise perimeter microneedles that surround one or more central microneedles. Thus, in any embodiment, registering a location of at least one microneedle can comprise registering the location of one or more perimeter microneedles.

Thus, in another aspect, the present invention provides a method of producing an article comprising one or more hollow microneedles. FIG. 8 shows a block diagram of one embodiment of a method 200 of producing an article comprising one or more hollow microneedles according to the present disclosure. The method 200 comprises the step 131 of molding a material to form a substrate having a plurality of microneedles, each microneedle having a first cavity extending into the body of the microneedle from the first side of the substrate and a second cavity extending into the body of the microneedle from the second side of the substrate, as described herein. The method 200 further comprises the step 133 of affixing the article. The article can be affixed, for example, to an apparatus as described hereinabove. After affixing the article to the apparatus, the method 200 further comprises the step 135 of registering the location of at least one microneedle, for example, as described hereinabove. It is contemplated that other means of registering the location of microscale objects known in the art may alternatively be used to register the location of at least one microneedle. After registering the location of the microneedles, the method 200 further comprises forming a hollow channel through one of the plurality of microneedles.

Forming the hollow channel comprises forming a channel between the first cavity of the microneedle and the second cavity of the microneedle. The channel is formed by any suitable method of removing at least a portion of the substrate material interposed between the first cavity and the second cavity to create a through-hole.

Thus, the channel can be formed in the microneedle using a variety of processes including piercing, mechanical microdrilling, highly-localized melting (e.g., laser-mediated melting), and ablation (e.g., using laser or e-beam ablation) processes. Any melting process further can comprise an ejection process (e.g., using pressurized gas) to remove melted material. Advantageously, ablation processes (e.g., laser ablation processes) can result in higher-quality (e.g., more uniform) channels.

In a preferred embodiment, a laser ablation (also known as "laser drilling") process is used to form the channel. Laser drilling of polymeric microneedles is described by Martanto et al. (Side-Opening Hollow Microneedles for Transdermal Drug Delivery , School of Chemical and Biomolecular Engineering, School of Electrical and Computer Engineering, Georgia Institute of Technology, Atlanta, Ga.), Aoyagi et al. (Laser fabrication of high aspect ratio thin holes on biodegradable polymer and its application to a microneedle , Sensors and actuators. A, Physical ISSN 0924-4247), and U.S. Pat. No. 6,881,203, which are incorporated herein by reference in their entirety.

Typically, laser drilling is accomplished by locally transferring energy from an intense laser beam into the material for the purpose of removing some of the material. This material removal can be achieved with one or more effects including heating, melting, ejecting, evaporating, ablating, decomposing, etc. These effects are initiated by the energy transfer from the intense beam. The ratio of the material removal and, thus, the efficiency of the drilling process is a function of the energy of photons, focal spot size, pulse duration, and pulse energy. The absorption properties, thermal properties, and $T_g$ (glass transition temperature) of the substrate material are considered when optimizing a laser ablation process. In addition, specific control handles for the process include, for example, the pulse duration, wavelength, repetition rate, total drilling time per microneedle, and energy per pulse.

Undesired energy transfer through the microneedle structure during laser drilling can result in deformation of the needle and loss of performance. Any of a variety of laser types can be used to form a hollow channel in a microneedle according to the present disclosure. In one aspect, laser types can be classified according to the minimum pulse duration the laser is capable of producing. Thus, the inventive process can uses an ultrafast laser (e.g., a femtosecond to picosecond laser) to remove substrate material from the microneedles. Alternatively, the inventive process can use a nanosecond laser (e.g., an excimer laser, solid-state laser) to remove substrate material from the microneedles. In some embodiments, the inventive process can use a laser having pulse durations longer than one nanosecond to remove substrate material from the microneedles. Preferably, the laser and process conditions used to remove substrate material from the microneedles are selected to minimize undesirable heat transfer throughout the microneedle structure.

A nonlimiting example of a laser that is suitable for use in a method of making an article according to the present disclosure is a SPECTRA PHYSICS master oscillator amplifier laser system available from Newport Corporation (Franklin, Mass.). The laser can generate a beam with femtosecond pulses having a wavelength of 800 nm, for example. It is contemplated that lasers having other wavelengths may be suitable for use with polymeric materials that are used to make a microneedle article according to the present disclosure. In some embodiments, a femtosecond laser having a wavelength of about 1000 nanometers can be used to form a channel between the first and second cavities of the microneedles. In some embodiments, a femtosecond laser having a wavelength of about 1500 nanometers can be used to form a channel between the first and second cavities of the microneedles.

In any embodiment, the laser can operate at a nominal pulse repetition rate of 1 kHz, for example. In any embodiment, the beam can pass through a power control unit comprising a rotary stage, half waveplate, and a polarizing beam splitter cube. In any embodiment, the drilling head can focus the laser beam through an appropriate microscope objective (e.g., 10× magnification, 0.2 Numerical Aperture). In any embodiment, the laser can be focused on the microneedle for a period of time sufficient to bore a channel through the microneedle from a point in the second cavity to a point in the first cavity. In any embodiment, the laser can be focused on the microneedle for a period of time sufficient to partially bore a channel (e.g., to bore a relatively narrow-diameter through-hole or to bore a channel that does not extend all of the way through the microneedle) from a point in the second cavity to a point in the first cavity. The process can be repeated several times (e.g., 2 times, 3 times, 4 times, 5 times, 6 times, 7 times, 8 times, at least 10 times) to increase the diameter of the channel between the first and second cavities. Optionally, the position of the laser beam path can be slightly offset each time (e.g., by moving the microneedle article relative to the laser beam or by moving the laser beam relative to the microneedle article, in order to expand and/or shape the channel being formed.

In any embodiment, the laser drilling time can be controlled to optimize the number of laser pulses required to create the channel and to minimize undesirable heat build-up in the microneedle. In any embodiment, the pulse duration can be about 100 femtoseconds to about 100 picoseconds, inclusive. In any embodiment, the pulse duration can be about 100 femtoseconds to about 10 picoseconds, inclusive. In any embodiment, the pulse duration can be about 100 femtoseconds to about 1 picosecond, inclusive. In any embodiment, the pulse duration can be about 1 picosecond to about 10 picoseconds, inclusive.

Figure 10:
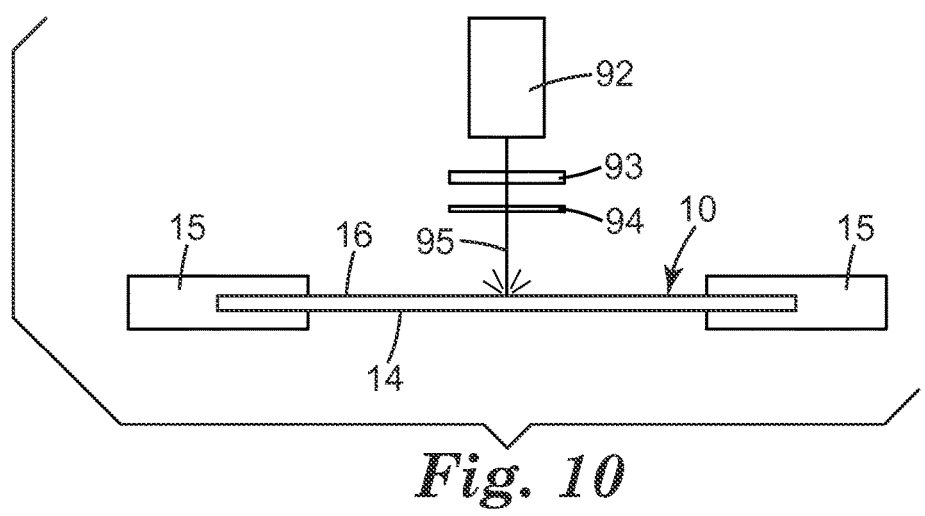
FIG. 10 is a schematic side view of one embodiment of a second subsystem for creating a through-hole in a microneedle, the subsystem being part of a system for forming a hollow channel through a microneedle according to the present disclosure.

FIG. 10 shows a schematic side view of one embodiment of a system for forming through-holes in the microneedle article 10 of FIG. 9. The system comprises the apparatus 15 of FIG. 9. The system further comprises a laser 92 facing the second side 16 of the article 10. Interposed between the laser 92 and the article 10 are a shutter 93 to control the exposure of the article to the laser beam 95 and an iris 94 to control the cross-sectional area of the laser beam 95. The imaging information from the system depicted in FIG. 9 is used to position individual microneedles (not shown) of the article 10 into the beam 95 of the laser 92, thereby creating a hollow bore through the each microneedle.

When removing relatively long portions of substrate material from the microneedles (e.g., ≥300 μm of material, ≥500 μm of material), the laser focal point (not shown) can be moved through each microneedle to create the through-hole. The process of moving the laser focal point can be accomplished by methods that are known in the art.

In any embodiment, the beam of the laser can be optically conditions and/or split using a variety of beam-conditioning or beamsplitting devices or techniques known in the art. In any embodiment, a mask element can be used as a part of the system for forming through-holes in the microneedle article. The mask element may permit the operator to 1) precisely control the area of the microneedle article that will be exposed to a laser beam and, optionally, 2) use a laser to simultaneously bore through-holes in a plurality of microneedles. The latter feature can substantially reduce the time necessary to form through-holes in an article comprising a relatively large number of microneedles.

In any embodiment, a laser and mask element can be used to form through-holes, or portions thereof, simultaneously in 2 microneedles. In any embodiment, a laser and mask element can be used to form through-holes, or portions thereof, simultaneously in 3 microneedles. In any embodiment, a laser and mask element can be used to form through-holes, or portions thereof, simultaneously in 4 microneedles. In any embodiment, a laser and mask element can be used to form through-holes, or portions thereof, simultaneously in 6 microneedles. In any embodiment, a laser and mask element can be used to form through-holes, or portions thereof, simultaneously in 8 microneedles. In any embodiment, a laser and mask element can be used to form through-holes, or portions thereof, simultaneously in 10 microneedles. In any embodiment, a laser and mask element can be used to form through-holes, or portions thereof, simultaneously in 12 microneedles. In any embodiment, a laser and mask element can be used to form through-holes, or portions thereof, simultaneously in 16 microneedles. In any embodiment, a laser and mask element can be used to form through-holes, or portions thereof, simultaneously in 18 microneedles. In any embodiment, a laser and mask element can be used to form through-holes, or portions thereof, simultaneously in 20 microneedles. In any embodiment, a laser and mask element can be used to form through-holes, or portions thereof, simultaneously in 30 microneedles. In any embodiment, a laser and mask element can be used to form through-holes, or portions thereof, simultaneously in >30 microneedles.

A mask element can be used with other beam-conditioning devices (e.g., microlenses). The mask element is fabricated from a material (e.g., a metal or metal-coated material such as quartz, for example) that substantially blocks the transmission of the laser beam. The mask element comprises optical apertures that permit the transmission of the laser beam therethrough. In any embodiment, the apertures may simply be holes (e.g., holes in a metal film, a metal coating, or metal sheet). The apertures can be configured with a pattern that is suitable for imaging the laser beam onto the second cavities. An excimer laser, for example, can be used cooperatively with a mask element to drill through-holes in one or more microneedles.

A laser beam passing through the beamsplitter is dispersed into beamlets that individually can be imaged onto a drilling surface (e.g., a cavity of a microneedle). In any embodiment, after passing the laser beam through a beamsplitting element, the resulting laser beamlets can be directed through an optical system comprising one or more mirrors and/or lenses (e.g., a demagnification projection lens) before being imaged on the microneedles to perform the laser drilling process.

In any embodiment, the mask element can comprise one or more aperture that is operationally coupled to an optical system to produce a laser beam image that is shaped and dimensioned to be coextensive with or fit within a shape defined by the second opening of a second cavity extending into a microneedle. The optical system may comprise elements that create a plurality of beams from a single beam (e.g., a lens array, a microlens array, phase mask, a beam-splitting cube, or a plate beamsplitter, or the like), one or more mirror, a projection lens (e.g. a demagnification projection lens), or a combination of two or more of the foregoing optical elements. In any embodiment, the mask element can comprise one or more aperture that is operationally coupled to an optical system to produce a laser beam image that is larger than the second opening of a second cavity extending into a microneedle.

In any embodiment, a beam from a laser can be split (e.g., using a phase mask, a microlens array, or other beam-splitting means known in the art. The resulting individual beamlets can then be redirected via one or more lenses, optionally in concert with one or more mirrors, to permit the simultaneous laser drilling of a plurality of microneedles.

After completing the laser drilling process, each microneedle in the article will comprise a through-hole extending from the first opening proximate the tip of the microneedle to the corresponding second opening on the opposite side of the article. The through-hole will have three distinct sections, each section having a surface topology corresponding to the process that was used to create the section.

Figure 11:
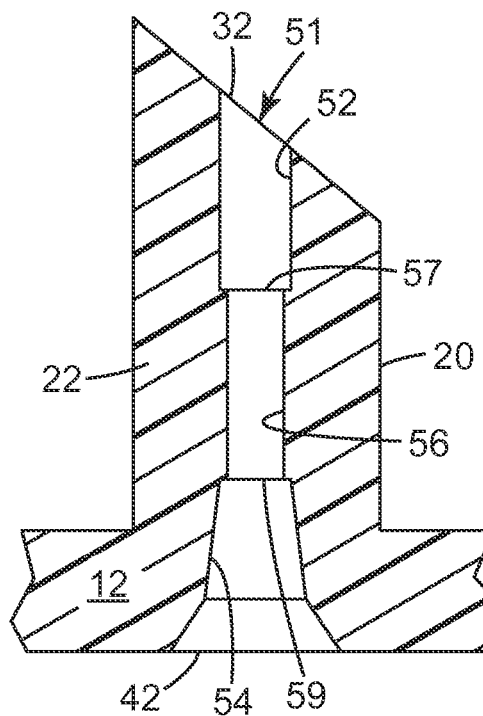
FIG. 11 is a schematic cross-sectional view of one embodiment of a hollow microneedle having a channel extending there through, the channel comprising a first channel segment, a second channel segment, and a third channel segment according to the present disclosure.

FIG. 11 shows a cross-sectional side view of one embodiment of portion of an article 10 comprising a hollow microneedle 20 produced by a method according to the present disclosure. The substrate 12 comprises a first side 14 from which the microneedle extends and a second side 16 opposite the first side. The microneedle 20 comprises a body 22 extending from a base 24 to a tip 26. The microneedle 20 further comprises a first opening 32, a second opening 42 and a channel 51 (i.e., a through-hole) extending from the first opening 32 to the second opening 42. The channel 51 comprises three separate channel segments (a first channel segment 52, a second channel segment 54, and a third channel segment 56 extending therebetween). The first channel segment 52 corresponds to a portion of the original first cavity (see first cavity 30 in FIG. 3). The second channel segment 54 corresponds to a portion of the original second cavity (see second cavity 40 in FIG. 3). Thus, both the first channel segment 52 and second channel segment 54 are produced by a molding process and, thus, the interior surface topology of each of the first and second channel segments substantially retains the shape and texture from the molding process. In contrast, the third channel segment 56 is produced by the drilling process described herein.

Disposed between the first channel segment 52 and the third channel segment 56 is a first transition locus 57. The first transition locus 57 is the point at which the third channel segment 56 joins the first channel segment 52. Optionally disposed between the second channel segment 54 and the third channel segment 56 is a second transition locus 59. Because the third channel segment 56 is formed by a different process (e.g., microdrilling, laser ablation) than the first channel segment 52 and second channel segment 54, which are both formed by a molding process, the interior surface topology of the third channel segment 52 is optically distinguishable from the interior surface topology of the first and second channel segments (52 and 54, respectively).

The first channel segment 52 has a first channel segment minimum diameter (not shown) at a location distal (i.e., not coincident with) the first transition locus 57. In addition, the third channel segment 56 has a third channel segment maximum diameter (not shown) at a location distal (i.e., not coincident with) the first transition locus 57. In any embodiment, the third channel segment maximum diameter is smaller than the first channel segment minimum diameter.

The third channel segment 56 has a third channel segment maximum diameter (not shown) at a location distal (i.e., not coincident with) the second transition locus 59. In addition, the second channel segment 54 has a second channel segment minimum diameter (not shown) at a location distal (i.e., not coincident with) the second transition locus 59. In any embodiment, the third channel segment maximum diameter is smaller than the second channel segment minimum diameter.

Embodiments

Embodiment A is an article, comprising:
  a substrate having first side and second side opposite the first side;
    wherein the first side comprises a first major surface that defines a base from which at least one microneedle extends;
    wherein the at least one microneedle comprises a body, a tip and a first cavity extending into the body;
    wherein the first cavity comprises an opening on the first side and a first terminus;
  wherein the second side comprises a second major surface comprising a second cavity that extends into the body of the at least one microneedle;
    wherein the second cavity comprises a second opening on the second side, and a second terminus;
  wherein the first terminus is spaced apart from the second terminus;
  wherein a straight line passing through the substrate can enter the substrate at a first point in the second cavity and exit the substrate at a second point in the first cavity.

Embodiment B is the article of Embodiment A, wherein the path of the straight line passes through the substrate only once.

Embodiment C is the article of Embodiment A or Embodiment B, wherein the first point is proximate the second terminus and the second point is proximate the first terminus Embodiment D is the article of any one of Embodiments A through C, wherein the at least one microneedle comprises a microneedle longitudinal axis, wherein the first opening is proximate the microneedle longitudinal axis.

Embodiment E is the article of any one of the preceding claims, wherein a shortest distance between the first cavity terminus and the second cavity terminus is about 1 micron to about 500 microns.

Embodiment F is the article of any one of the preceding claims, wherein the at least one microneedle comprises an array of a plurality of microneedles.

Embodiment G is an article, comprising:
  a substrate having first side and second side opposite the first side,
    wherein the first side comprises a first major surface having at least one microneedle extending therefrom, the at least one microneedle comprising a body and a first opening;

wherein the second side comprises a second major surface having a second opening; and
a channel extending from the first opening to the second opening, the channel having a first channel segment extending from the first opening, a second channel segment extending into the substrate from the second opening, and a third channel segment extending between the first channel segment and the second channel segment;
wherein the first channel segment has a first interior surface topology, the second channel segment has a second interior surface topology, and the third channel segment has a third interior surface topology;
wherein the third interior surface topology is optically distinguishable from the first interior surface topology.

Embodiment H is the article of Embodiment G, wherein the first channel segment extends from the first opening to a first transition locus in the body of the at least one microneedle.

Embodiment I is the article of Embodiment F or Embodiment G, wherein the second channel segment extends from the second opening to a second transition locus in the body of the at least one microneedle.

Embodiment J is the article of any one of embodiments G through I, wherein the third interior surface topology is optically distinguishable from the first interior surface topology and the second interior surface topology.

Embodiment K is article of any one of Embodiments G through J, wherein a maximum diameter of the third channel segment at a location distal the first transition locus is smaller than a minimum diameter of the first channel segment at a location distal the first transition locus.

Embodiment L is the article of any one of Embodiments G through J, wherein a maximum diameter of the third channel segment at a location distal the second transition locus is smaller than a minimum diameter of the second channel segment at a location distal the second transition locus.

Embodiment M is the article of any one of the preceding Embodiments, wherein the substrate is formed of a material selected from the group consisting of polycarbonate, cyclic olefin copolymer, liquid crystal polymer, polyacrylate, acrylate copolymer, polystyrene, polypropylene, polyethylene, polyester, polyamide, polyamide imide, polyetheretherketone, polyetherimide, polybutylene terephthalate, polyphenyl sulfides, acetals, polyethylene terephthalates polyvinyl chloride, polymethylmethacrylate, acrylonitrile-butadiene styrene, or combinations thereof.

Embodiment N is the article of any one of Embodiments G through M, wherein the channel is spaced apart from the tip of the microneedle.

Embodiment O is the article of any one of the preceding claims, wherein the at least one microneedle has a height extending from the base to the tip, wherein the height is about 100 microns to about 1500 microns, inclusive.

Embodiment P is the article of any one of the preceding claims, wherein the aspect ratio of the each microneedle in the plurality of microneedles is about 2:1 to about 5:1, inclusive.

Embodiment Q is a method, comprising:
molding a material to form a substrate comprising:
a first side comprising a first major surface that defines a base from which a plurality of microneedles extend;
wherein each microneedle of the plurality of microneedles comprises a body, a tip and a first cavity extending into the body; and
a second side opposite the first side, the second side having a second major surface that comprises a plurality of second cavities, each second cavity extending into a body of one of the plurality of microneedles;
wherein a straight line passing through the substrate can enter the substrate at a first point in the first cavity and exit the substrate at a second point in the second cavity;
affixing the substrate;
registering a location of at least one microneedle; and
forming a hollow channel through one of the plurality of microneedles, wherein forming a hollow channel comprises forming a channel between the first cavity and the second cavity.

Embodiment R is the method of Embodiment Q, wherein the straight line passes through the substrate only once.

Embodiment S is the method of Embodiment Q or Embodiment R, wherein the first cavity comprises a first opening and a first terminus opposite the first opening, wherein the second cavity comprises a second opening and a second terminus opposite the second opening, wherein the straight line passing through the substrate can enter the substrate at a first point at the first terminus and exit the substrate at a second point at the second terminus.

Embodiment T is the method of any one of Embodiments Q through S, wherein the plurality of microneedles comprises an array of microneedles, wherein the array comprises perimeter microneedles, wherein registering a location of at least one microneedle comprises registering the location of the perimeter microneedles.

Embodiment U is the method of any one of Embodiments Q through T, wherein registering a location of at least one microneedle comprises registering the location of each microneedle of the plurality of microneedles.

Embodiment V is the method of any one of Embodiments Q through U, wherein molding a material comprises microreplicating the material.

Embodiment W is the method of any one of Embodiments Q through V, wherein forming a hollow channel comprises using an ablation process, a melting process or a mechanical drilling process.

Embodiment X is the method of Embodiment W, wherein the ablation process comprises a laser ablation process.

Embodiment Y is the method of Embodiment W or Embodiment X, further comprising:
using a mask element to target the ablation process.

Embodiment Z is the method of Embodiment Y, wherein the mask element comprises a mask aperture that is operationally coupled to an optical system to produce a laser beam image that is shaped and dimensioned to be coextensive with or fit within a shape defined by the second opening.

Embodiment AA is the method of Embodiment Y, wherein the mask element comprises a mask aperture that is operationally coupled to an optical system to produce a laser beam image that is larger than the second opening.

Embodiment BB is the method of any one of Embodiments Q through AA, further comprising the step of imaging at least one microneedle of the plurality of microneedles.

Embodiment CC is the method of Embodiment BB, wherein imaging at least one microneedle comprises directing electromagnetic radiation toward the first major surface and using an imaging device to capture an image of the second major surface or directing electromagnetic radiation toward the second major surface and using an imaging device to capture an image of the first major surface.

Embodiment DD is the method of any one of Embodiments Q through CC, wherein forming a hollow channel through one of the plurality of microneedles comprises using an excimer laser to form the hollow channel.

Embodiment EE is the method of any one of Embodiments Q through DD, wherein forming a hollow channel through one of the plurality of microneedles further comprises simultaneously forming a hollow channel in two or more of the microneedles in the plurality of microneedles.

Embodiment FF is a method, comprising:
molding a material to form a substrate comprising:
a first major surface comprising a plurality of microneedles extending there from, each microneedle comprising a first cavity; and
a second major surface opposite the first major surface, the second major surface comprising a plurality of second cavities;
wherein molding the material comprises forming a thinned region of the material between the first cavity and the second cavity;
wherein a straight line passing through the substrate can enter the substrate at a first point in the second cavity and exit the substrate at a second point in the first cavity; and
directing electromagnetic radiation toward the first major surface and using an imaging device to capture an image of the second major surface or directing electromagnetic radiation toward the second major surface and using an imaging device to capture an image of the first major surface; and
using the image to process two or more microneedles of the plurality of microneedles.

Embodiment GG is the method of Embodiment FF, wherein the straight line passes through the substrate only once.

Embodiment HH is the method of Embodiment FF or Embodiment GG, wherein each of the plurality of microneedles comprises a body, molding a material to form a substrate comprises molding the material such that each cavity of the plurality of second cavities extends into the body of one of the plurality of microneedles.

Embodiment II is the method of any one of Embodiments FF through HH, wherein processing two or more microneedles comprises creating through-hole between the first and second cavities of a plurality of microneedles.

Embodiment JJ is the method of any one of Embodiments FF though II, wherein processing two or more microneedles comprises applying a composition to a plurality of microneedles.

Embodiment KK is the method of Embodiment JJ, wherein applying a composition to the microneedles comprises applying a composition to the microneedles substantially without applying the composition to other portions of the first major surface.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Example 1

The microneedle arrays of this Example were prepared from polymeric material using standard injection molding procedures. For each microneedle array pattern, a first mold half was prepared from a master array. The master array was formed using the 2-photon lithography fabrication method described in U.S. patent application Publication No. US2009/0099537 (DeVoe et al.), which is incorporated herein by reference in its entirety. The master array was then electroplated with nickel (2.79 mm thick) according to the procedure described in Example 6 of DeVoe et al. to create the inverse (or negative) form of the master that was used as the first mold half. The first mold half served as a template to define the pattern of the microneedles in the molded array, the first major surface of the base portion of the array, the external shape of the microneedles, and the first cavity with a first opening located proximate the tip of each microneedle (with the cavity extending into the microneedle structure toward the base). For some of the microneedles prepared in this example, a cross-hair feature was machined into the top surface of each projection of the mold. This feature was used to define a first cavity in order to easily visualize the surface of the polymeric material at the terminus of each first cavity.

The second mold half was machined from a steel plate. The second mold half contained cylindrical projections emerging from a planar surface. The projections had flat tips that were positioned and spaced so as to align each projection with a corresponding cavity in the first mold half. The projections of the second mold half served as a template to define the second cavity with a second opening located at the base of each microneedle of the molded array (with the cavity extending into the microneedle structure toward the tip). The planar surface from which the projections emerged served to define the second major surface of the base portion of the molded array.

The first and second mold halves were installed in a mold base in a 60-ton injection molding press (Sodick Plustech LA 60, Sodick Plustech Co., Yokohama, Japan). As is common in the art, the parting line of the mold assembly had both primary and secondary vents for general air evacuation during injection of the polymeric material. Vectra MT1300 liquid crystal polymer (LCP) pellets (Ticona Engineering Polymers, Florence, Ky.) were loaded into a reciprocating screw and heated until molten. The first mold half and second mold half were heated to a temperature (hereafter referred to as the "mold temperature at injection") of 200° F. (93.3° C.). The molding cycle was initiated by closing the first mold half with the second mold half. The molds were clamped together with approximately 20 to 60 tons of force. In the clamped position, the projections of the second mold half did not contact any surface of the first mold half. A first portion (approx. 50-95% of the part size volume) of the total amount of material from the reciprocating screw was injected into the mold chamber at a fixed velocity (hereafter referred to as the "injection velocity") of 7 inches/second (17.8 cm/second). After injecting the first portion of material, the process was switched from an injection-driven to a pressure-driven mode by applying a fixed pressure (hereafter referred to as the "pack pressure") of 13,500 psi (93,079 kilopascal) to force the remainder of the molten material into the negative mold insert. The pack pressure was applied for a fixed time (hereafter referred to as the "hold time") of 5 seconds. The pack pressure was subsequently released and the mold chamber was cooled to an ejection temperature set below the softening temperature of LCP. The mold chamber was opened and the microneedle array was ejected.

Example 2

As an alternative, the molded microneedle arrays described in Example 1 were prepared using a mold assembly prepared from three mold sections with each section machined from steel. The first mold section contained projections that defined the beveled shape of the needle tip in the molded array. Each projection in the first mold section had a further cylindrical extension that defined the first cavity with a first opening in the molded product. The second mold section served as a template to define the pattern of the MNs in the molded array, the first surface of the base portion of the molded array, and the external shape and size of the microneedles in the molded array. The third mold section contained cylindrical projections emerging from a planar surface with the projections defining the second cavity and second opening located at the base of each microneedle in the molded array. The planar surface from which the projections emerged served to define the second major surface of the base portion of the molded array. As an option, a cross-hair feature could be machined into the top surface of each projection.

The first and second mold sections were assembled to form a tight fit by inserting the projections of the first mold section into the corresponding openings in the second mold section. The assembled first and second mold sections formed the first mold half. The third mold section was used as the second mold half. The first and second mold halves were installed in a mold base in a 60-ton injection molding press (Sodick Plustech LA 60) and the molded arrays were prepared using the same procedure and conditions as described in Example 1.

Example 3

The microneedle array was prepared by the injection molding method described in Example 2. The array was prepared in the shape of a square approximately 1.6 cm$^2$ in area. The base portion of the array was about 0.8 mm thick. The array featured 16 microneedles arranged in a 4 by 4 square pattern centered on the array. The microneedles extended from the first major surface of the base portion of the array. Each microneedle was in the shape of a conventional hypodermic needle with a rounded beveled tip. The spacing between neighboring microneedles was about 2 mm (as measured from tip to tip). Each microneedle had a height of about 1000 microns with an aspect ratio of about 3:1. The cavity proximal to the tip in each microneedle was about 140 microns in diameter, while the cavity located at the base in each microneedle was about 100 microns in diameter. The solid section of LCP separating the floors of the two cavities was about 25 microns thick and was located about 400 microns from the tip of each microneedle.

A laser drilling procedure was used to remove enough of the LCP material located between the cavities of the microneedles to create a hollow trough bore in each microneedle. An excimer laser micromachining system with high resolution imaging optics (VarioLas Pro 248 system, Coherent Inc., Santa Clara, Calif.) and integrated with a Compex Pro 110F krypton-fluoride laser (Coherent, Inc.) was used for drilling. The laser was operated at a wavelength of 248 nm. The laser generated 25 nanosecond pulses of up to 400 mJ per pulse with a maximum repetition rate of 100 Hz. The beam from the laser was homogenized with two lenslet arrays and directed to illuminate a mask element containing apertures. The light passing through the apertures was imaged with a 7× demagnification projection lens. The projection module was equipped with a CCD camera (model KS722UP, NET New Electronic Technology GmbH, Finning, Germany) and vision system suitable for microneedle-beamlet registration. The camera and vision system were used to position the laser drilling head relative to the microneedle array in a precise manner.

The microneedle array was attached to a 3-axis (XYZ) stage combined with a rotation stage (PI miCos GmbH, Eschbach, Germany). The microneedle array was positioned so that the second major surface of the base portion of the array was facing toward the laser beam. A UV-quartz mask with an Anti-reflective-Cr coating was used as the mask element. The mask element contained four apertures, each aperture having a diameter of 525 microns. While passing through the mask apertures, the laser beam was split into a plurality of beamlets. The beamlets were passed through the 7× demagnification projection lens and a demagnified image of each aperture was projected onto one of the microneedles. The diameter of the demagnified image of each aperture was about 75 microns. The image of the aperture pattern from the mask element was projected on the microneedle array so that each one of the projected demagnified aperture images was oriented to align with a different microneedle of the array. The alignment was configured to project the demagnified image completely within the border of the cavity formed in the corresponding microneedle. With the mask element in position, the laser drilling program was initiated. The laser was operated at a repetition rate of 100 Hz and the fluence was set to 500 mJ/cm$^2$. Approximately 120 to 140 pulses were required to form a through hole (or channel) in each of the four targeted microneedles. The stage was then manually moved to the next set of four microneedles and the procedure of beamlet-microneedle registration followed by laser drilling was repeated. The procedure was continued until all of the microneedles of the array had been processed. Approximately 1.5 seconds were needed to complete the laser drilling of a set of four microneedles (removing a thickness of 25 microns of material from each microneedle).

A total of thirty arrays were processed using the described conditions. A Leica Wild M10 stereo microscope (Leica Microsystems GmbH, Wetzlar, Germany) with both back and top lighting was used to examine each array at a magnification setting of 8× to 80×. For ninety percent of the arrays, there was no deformation or damage to the tips or overall structure of any of the microneedles of the arrays. In all of the microneedles of the undamaged arrays, a borehole (or channel) was successfully drilled through the solid section of LCP material separating the floors (i.e., "termini") of the two cavities.

A subset of three arrays was randomly selected from the undamaged arrays and an Olympus BH-2 optical microscope (Olympus Corporation, New Hyde Park, N.Y.) with a 20× objective was used to measure the diameters of the boreholes created by the drilling operation. All 16 microneedles in an array were measured (n=48). The diameters of the boreholes ranged from 70 to 76 microns.

Example 4

The same materials and procedure as described in Example 3 were used with the exception that a mask element containing four apertures with the demagnified image of the laser beamlet passing through each aperture having a diameter of 150 microns (instead of 75 microns as in Example 3) was used. The image of the aperture pattern from the mask element was projected on the microneedle array so that each one of the projected aperture images was aligned with a different microneedle of the array. Since the diameter of each projected aperture image was larger than the diameter of the opening of the cavity in each microneedle, the cavity of each microneedle was aligned to be completely within the border defined by the corresponding projected aperture image. With the mask element in position, the laser drilling program was initiated. The laser was operated at a repetition rate of 100 Hz and the fluence was set to 500 mJ/cm$^2$. Approximately 120 to 140 pulses were required to form a through hole (or channel) in each of the four targeted microneedles. The stage was then manually moved to the next set of four microneedles and the procedure of beamlet-microneedle registration followed by laser drilling was repeated. The procedure was continued until all of the microneedles of the array had been processed. Approximately 1.5 seconds were needed to complete the laser drilling of a set of four microneedles.

A total of ten arrays were processed using the described conditions. A Leica Wild M10 stereo microscope (Leica Microsystems GmbH) with both back and top lighting was used to examine each array at a magnification setting of 8× to 80×. For eighty percent of the arrays, there was no deformation or damage to the tips or overall structure of any of the microneedles of the arrays. In all of the microneedles of the undamaged arrays, a borehole (or channel) was successfully drilled through the solid section of LCP material separating the floors of the two cavities.

A subset of three arrays was randomly selected from the undamaged arrays and an Olympus BH-2 optical microscope (Olympus Corporation) with a 20× objective was used to measure the diameters of the boreholes created by the drilling operation. All 16 microneedles in an array were measured (n=48). The diameters of the boreholes ranged from about 97 to 100 microns. For each microneedle, a very small amount of material in the second cavity, proximate the second opening, was removed by the laser.

Example 5

The same microneedle array as described in Example 3 was used. A femtosecond laser drilling procedure was used to remove enough of the LCP material located between the cavities of the microneedles to create a hollow trough bore in each microneedle. A Hurricane laser system (Spectra-Physics, Santa Clara, Calif.) was operated at a wavelength of 800 nm and a pulse duration of 300 femtoseconds (fs). The laser beam was passed through a power control unit and then directed by a set of 3 mirrors to a 3× beam expander. An iris with a 10 mm aperture was used behind the expander to transmit only the central part of the beam. The beam was finally passed through a 75 mm focal point lens before being directed onto the targeted portions of the array. The lens was mounted in a holder attached to a Z-axis positioning stage (Aerotech Inc., Pittsburgh, Pa.). The pulse repetition rate was set at 1 kHz. The average power was set at 130 to 160 mW (measured after the laser beam passed through the lens).

The microneedle array was attached to a 2-axis (XY) positioning stage (Aerotech Inc., Pittsburgh, Pa.). The microneedle array was positioned so that the second major surface of the base of the array was facing toward the laser beam. The position of each microneedle in the array was determined using a Prosilica Model EC1600 CCD camera (Allied Vision Technologies, Inc., Burnaby, Canada) with a large field F-Theta 0.4× magnification objective (model NT56-677, EO Edmund Optics, Barrington, N.J.). The motion control and image recognition programs were developed using LabVIEW 2012 with the NI Vision Development Module 2011 (National Instruments, Austin, Tex.). The camera was oriented with respect to the array in the same manner as the laser beam. The microneedle array was imaged with transmitted light (i.e. the source of white light was positioned on the side of the array opposite the camera position and the light was directed toward the camera). In this set-up, the solid section of LCP separating the two cavities of each microneedle was thin enough that a sufficient amount of light was transmitted through the solid section for the image recognition system to detect the light. The relatively-bright spots of transmitted light were used by the image recognition system to identify the location in each microneedle of the array for laser drilling. After the image recognition system determined all of the microneedle locations on the array, the lateral coordinate drilling positions were sent to the main computer and the automated laser drilling program was initiated. The laser drilling program automatically moved the XY stage to position the array in the correct drilling locations. The drilling time was approximately 0.2 seconds per microneedle. Approximately 5 to 6 seconds (including registration) were needed to complete the drilling of all the microneedles in the array.

An Olympus BH-2 optical microscope (Olympus Corporation) with a 20× objective was used to measure the diameters of the boreholes created by the drilling operation in an array. All 16 microneedles in the array were measured. The diameters of the boreholes ranged from about 50 to 65 microns.

Example 6

The microneedle array was prepared from by the injection molding method described in Example 2. The array was prepared in the shape of a square approximately 1.6 cm$^2$ in area. The base portion of the array was about 0.8 mm thick. The array featured 12 microneedles (arranged in a square pattern with four microneedles defining each side of the square) centered on the array. The microneedles extended from the first major surface of the base portion of the array. Each microneedle was in the shape of a conventional hypodermic needle with a rounded beveled tip. The spacing between neighboring microneedles was about 2 mm (as measured from tip to tip). Each microneedle had a height of about 1500 microns with an aspect ratio of about 3:1. The two cavities created in each microneedle by the molding procedure each had a diameter of about 100 microns. The solid section of LCP separating the floors of the two cavities was about 50 microns thick and was located about 400 microns from the tip of each microneedle.

A femtosecond laser drilling procedure was used to remove enough of the LCP material located between the cavities of the microneedles to create a hollow trough bore in each microneedle. A Solstice laser system (SpectraPhysics, Santa Clara, Calif.) was operated at a wavelength of 800 nm and a pulse duration of 300 fs. The laser beam was passed through a power control unit and then directed by a set of 3 mirrors to a 3× beam expander. An iris with a 10 mm aperture was used behind the expander to transmit only the central part of the beam. The beam was finally passed through a 60 mm focal point lens before being directed onto the targeted portions of the array. The lens was mounted in a holder attached to a Z-axis positioning stage (Aerotech Inc.). The pulse repetition rate was set at 1 kHz. The average power was set at 130 to 160 mW (measured after the laser beam passed through the lens).

The microneedle array was attached to a 2-axis (XY) positioning stage (Aerotech Inc.). The microneedle array was positioned so that the second major surface of the base of the array was facing toward the laser beam. The position of each microneedle in the array was determined using a CCD camera (model acA1300-30 gm, Basler Inc., Exton, Pa.) with a 1.5 mm by 1.5 mm field of view and an image recognition software program (VPRO-MAX software, Cognex Inc., Natick, Mass.). The camera was positioned on the side of the array opposite the laser beam and the light source was oriented with respect to the array in the same manner as the laser beam. The microneedle array was imaged with transmitted light (i.e. the source of white light was directed toward the camera). In this set-up, the solid section of LCP separating the two cavities of each microneedle was thin enough that a sufficient amount of light was transmitted through the solid section for the image recognition system to detect the light. The relatively-bright spots of transmitted light were used by the vision system to identify the location in each microneedle of the array for laser drilling. After the image recognition system determined all of the microneedle locations on the array, the lateral coordinate drilling positions were sent to the main computer and the automated laser drilling program was initiated. The laser drilling program automatically moved the XY stage to position the array in the correct drilling locations. The drilling time was approximately 0.25 seconds per microneedle. Approximately 25 seconds (including registration) were needed to complete the drilling of all the microneedles in the array.

A total of 50 arrays were processed using the described conditions. A stereo microscope (Thermo Fisher Scientific, Waltham, Mass.) with both back and top lighting was used to examine each array at a magnification of 25×. No deformation or damage to the tips or overall structure of any of the microneedles of the arrays was observed. In all of the microneedles of the arrays, a borehole (or channel) was successfully drilled through the solid section of LCP separating the floors of the two cavities.

A subset of three arrays was randomly selected and a NEXIV-K6555 optical microscope (Nikon Metrology Inc., Brighton, Mich.) operated at a magnification of 21× was used to measure the diameters of the boreholes created by the drilling operation. All 16 microneedles in an array were measured. The average diameter of the boreholes and the standard deviation was recorded for each array. For the three sample arrays, the average borehole diameter ranged from 75.7 to 77.4 microns with a standard deviation that ranged from 3.4 to 4.3 microns.

Example 7

The microneedle array was prepared from by the injection molding method described in Example 1. The array was prepared in the shape of a circle approximately 1.25 cm in diameter. The base portion of the array was about 0.8 mm thick. The array featured 18 microneedles arranged in pattern of two concentric hexagons centered on the array. The perimeter of the outer hexagon was composed of twelve evenly spaced microneedles and the perimeter of the inner hexagon was composed of six evenly spaced microneedles. The microneedles extended from the first major surface of the base portion of the array. Each microneedle was in the shape of a conventional hypodermic needle with a pointed beveled tip. The spacing between neighboring microneedles was about 2 mm (as measured from tip to tip). Each microneedle had a height of about 900 microns with an aspect ratio of about 3:1. The two cavities created in each microneedle by the molding procedure each had a diameter of about 80 microns. The floor of the cavity that was proximal to the tip in each microneedle was about 330 microns from the tip. The solid section of LCP separating the floors of the two cavities was about 500 microns thick. A femtosecond laser drilling procedure was used to remove enough of the LCP material located between the cavities of the microneedles to create a hollow trough bore in each microneedle. A Solstice laser system (SpectraPhysics, Santa Clara, Calif.) was operated at a wavelength of 800 nm and a pulse duration of 300 fs. The laser beam was passed through a power control unit and then directed by a set of 3 mirrors to a 3× beam expander. An iris with a 10 mm aperture was used behind the expander to transmit only the central part of the beam. The beam was finally passed through a 60 mm focal point lens before being directed onto the targeted portions of the array. The lens was mounted in a holder attached to a Z-axis positioning stage (Aerotech Inc.). The pulse repetition rate was set at 1 kHz, and the power setting was set at 130 to 160 mW.

The microneedle array was attached to a 2-axis (XY) positioning stage (Aerotech Inc.). The microneedle array was positioned so that the second major surface of the base of the array was facing toward the laser beam. The position of each microneedle in the array was determined using a CCD camera (model acA1300-30 gm, Basler Inc) with a 1.5 mm by 1.5 mm field of view and an image recognition software program (VPRO-MAX software, Cognex Inc). The camera and the light source were both positioned on the side of the array opposite the laser beam. The microneedle array was imaged with reflected light. The cross-hair feature that was incorporated during the molding process into the solid section of LCP separating the two cavities was used by the image recognition system to identify the location in each microneedle of the array for laser drilling. After the image recognition system determined all of the microneedle locations on the array, the lateral coordinate drilling positions were sent to the main computer and the automated laser drilling program was initiated. The laser drilling program automatically moved the XY stage to position the array in the correct drilling locations. The drilling time was approximately 1 second per microneedle. Approximately 45 seconds were needed to complete the drilling of all the microneedles in the array.

A total of 1000 arrays were processed using the described conditions. A stereo microscope (Thermo Fisher Scientific) with both back and top lighting was used to examine each array at a magnification of 25×. For 963 of the arrays, there was no deformation or damage to the tips or overall structure of any of the microneedles of the arrays. In all of the microneedles of the undamaged arrays, a borehole (or channel) was successfully drilled through the solid section of LCP separating the floors of the two cavities.

A subset of 79 arrays was randomly selected from the 963 undamaged arrays and a NEXIV-K6555 optical microscope (Nikon Metrology Inc) operated at a magnification of 21× was used to measure the diameter of the borehole created by the drilling operation. All 18 microneedles in an array were measured. The average diameter of the boreholes and the standard deviation was recorded for each array. For the 79 sample arrays, the average borehole diameter ranged from 38.3 to 42.6 microns with a standard deviation that ranged from 1.0 to 3.5 microns.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

What is claimed is:

1. An article, comprising:
a substrate having first side and second side opposite the first side;
wherein the first side comprises a first major surface that defines a base from which at least one microneedle extends;
wherein the at least one microneedle comprises a body, a tip and a first cavity extending into the body;
wherein the first cavity comprises an opening on the first side and a first terminus located within the body of the microneedle;
wherein the second side comprises a second major surface comprising a second cavity that extends into the body of the at least one microneedle;
wherein the second cavity comprises a second opening on the second side, and a second terminus located within the body of the microneedle;
wherein the first terminus is spaced apart from the second terminus;
and a thinned region disposed between the first cavity and the second cavity in the body of the microneedle;
wherein a straight line passing through the substrate can enter the substrate at a first point in the second cavity and exit the substrate at a second point in the first cavity.

2. The article of claim 1, wherein the first point is proximate the second terminus and the second point is proximate the first terminus.

3. The article of claim 1, wherein a shortest distance between the first cavity terminus and the second cavity terminus is about 1 micron to about 500 microns.

4. The article of claim 1, wherein:
the first cavity defines a first channel segment;
the second cavity defines a third channel segment; and
further comprising a third channel segment extending through at least a portion of the thinned region between the first terminus and the second terminus
wherein the first channel segment has a first interior surface topology, the second channel segment has a second interior surface topology, and the third channel segment has a third interior surface topology;
wherein the third interior surface topology is optically distinguishable from the first interior surface topology.

5. The article of claim 4, wherein the first channel segment extends from the first terminus to a first transition locus in the body of the at least one microneedle.

6. The article of claim 4, wherein the second channel segment extends from the second terminus to a second transition locus in the body of the at least one microneedle.

7. The article of claim 4, wherein the third interior surface topology is optically distinguishable from the first interior surface topology and the second interior surface topology.

8. The article of claim 4, wherein a maximum diameter of the third channel segment at a location distal to the second transition locus is smaller than a minimum diameter of the second channel segment at a location distal the second transition locus.

9. The article of claim 4, wherein the aspect ratio of the each microneedle in the plurality of microneedles is about 2:1 to about 5:1, inclusive.

10. A method, comprising:
molding a material to form the article of claim 1,
affixing the substrate;
registering a location of at least one microneedle; and
forming a hollow channel through one of the plurality of microneedles, wherein forming a hollow channel comprises forming a channel through the thinned region between the first cavity and the second cavity.

11. The method of claim 10, wherein the first cavity comprises a first opening and a first terminus opposite the first opening, wherein the second cavity comprises a second opening and a second terminus opposite the second opening, wherein the straight line passing through the substrate can enter the substrate at a first point at the first terminus and exit the substrate at a second point at the second terminus.

12. The method of claim 10, wherein the plurality of microneedles comprises an array of microneedles, wherein the array comprises perimeter microneedles, wherein registering a location of at least one microneedle comprises registering the location of the perimeter microneedles.

13. The method of claim 10, wherein forming a hollow channel comprises using an ablation process, a melting process, or a mechanical drilling process, wherein the ablation process comprises a laser ablation process, wherein the method further comprises using a mask element or beam-splitting element to target the ablation process.

14. The method of claim 10, further comprising the step of imaging at least one microneedle of the plurality of microneedles.

15. The method of claim 14, wherein imaging at least one microneedle comprises directing electromagnetic radiation toward the first major surface and using an imaging device to capture an image of the second major surface or directing electromagnetic radiation toward the second major surface and using an imaging device to capture an image of the first major surface.

16. The method of claim 10, wherein forming a hollow channel through one of the plurality of microneedles further comprises simultaneously forming a hollow channel in two or more of the microneedles in the plurality of microneedles.

17. A method, comprising:
molding a material to form an article of claim 1, and
directing electromagnetic radiation toward the first major surface and using an imaging device to capture an image of the second major surface or directing electromagnetic radiation toward the second major surface and using an imaging device to capture an image of the first major surface; and
using the image to process two or more microneedles of the plurality of microneedles.

18. The method of claim 17, wherein each of the plurality of microneedles comprises a body, wherein molding a material to form a substrate comprises molding the material such that each cavity of the plurality of second cavities extends into the body of one of the plurality of microneedles.

19. The method of claim 17, wherein processing two or more microneedles comprises creating through-hole between the first and second cavities of a plurality of microneedles.

20. The method of claim 17, wherein processing two or more microneedles comprises applying a composition to a plurality of microneedles.

\* \* \* \* \*